United States Patent [19]
Ding et al.

[11] Patent Number: 5,985,590
[45] Date of Patent: *Nov. 16, 1999

[54] **EXPRESSION OF *CARCINOSCORPIUS ROTUNDICAUDA* FACTOR C IN EUKARYOTES**

[75] Inventors: Jeak Ling Ding; Bow Ho, both of Singapore, Singapore

[73] Assignee: National University of Singapore, Singapore

[*] Notice: This patent is subject to a terminal disclaimer.

[21] Appl. No.: 08/877,620

[22] Filed: Jun. 18, 1997

Related U.S. Application Data

[60] Division of application No. 08/596,405, Feb. 2, 1996, Pat. No. 5,858,706, which is a continuation-in-part of application No. 08/296,014, Aug. 19, 1994, Pat. No. 5,716,834.

[51] Int. Cl.⁶ .................................................. C12Q 1/37
[52] U.S. Cl. .............................. 435/23; 435/7.9; 435/7.1; 435/7.2; 435/7.72; 435/219; 435/68.1; 530/350; 530/381
[58] Field of Search .............................. 435/23, 7.9, 7.1, 435/7.2, 7.72, 219, 68.1; 530/350, 381

[56] References Cited

U.S. PATENT DOCUMENTS

| | | | |
|---|---|---|---|
| 4,322,217 | 3/1982 | Dikeman | 23/230 |
| 4,906,567 | 3/1990 | Connelly | 435/7 |
| 5,082,782 | 1/1992 | Gibson, III et al. | 435/240.2 |
| 5,316,911 | 5/1994 | Baek et al. | 435/7.9 |
| 5,550,030 | 8/1996 | Tanaka et al. | 435/23 |
| 5,591,628 | 1/1997 | Baek et al. | 435/240.26 |

OTHER PUBLICATIONS

Navas III et al. (1988) 5 FAOB Congress, MO:19.
Ding et al (1993) *Biochimica et Biophysica Acta* 1202:149–156.
Roopashree et al., Microbiology in the Nineties, pp. 380 (1994).
Chai et al., Proceedings of the 4th Pacific Rim Biotech. Conference, Melbourne, pp. 129–130 (Feb. 1995).
Roopashree et al., Proceedings of the 4th Pacific Rim Biotech. Conference, Melbourne, pp. 131–132 (Feb. 1995).
Ding et al., Proceedings of the 4th Pacific Rim Biotech. Conference, Melbourne, pp. 345–346 (Feb. 1995).
S. D. Roopashree et al., Biochmistry and Molecular Biology International, 35:841–849 (Apr. 1995).
Ding et al. (1993) *Cytobios* 75:21–32.
Muta et al. (1991) J. Biol. Chem. vol. 266, pp 6554–6561.
Romanos et al.(1992) Yeast, vol. 8, pp. 423–488.
Ho (1983) *Microbios Letters* 24:81–84.
Ho et al. (1985) *Proc. 1st Intl. Cong. Singapore Soc. Microbiol*, pp. 664–669.
Kim et al. (1987) Singapore Society for Microbiology, 1987 Annual Scientific Meeting, p. 21.
Ding et al. (1988) *Cytobios* 55:147–154.
Kim et al. (1988) 7th FAOB Symposium, POS–F–01.
Yeo et al. (1989) Second SSM International Congress for Microbiology, BE8.
Navas III et al. (1990) *Biochemistry International* 21(5):805–813.
B. Ho et al. (1993) *Biochemistry and Molecular Biology International* 29(4) :687–694.
Ding et al., Essays in Zoology, pp. 337–341 (1990).
J.L. Ding et al., Molecular Marine Biology and Biotechnology, 4:90–103 (1995).

*Primary Examiner*—Charles L. Patterson, Jr.
*Assistant Examiner*—Enrique D. Longton
*Attorney, Agent, or Firm*—Birch, Stewart, Kolasch & Birch, LLP

[57] ABSTRACT

CrFC21 cDNA was cloned into two mammalian vectors: pCIneo and pCDNAI, both of which carry the strong CMV promoter for expression in mammalian cell lines. Various CrFC cDNA constructs transformed into *P. pastoris* and *S. cerevisiae* were expressed to yield full-length recombinant Factor C (rCrFC) protein of ~130 kDa which is immunoreactive. The rCrFC is expressed in an intracellular, insoluble form. Intracellular localization of the nascent protein provides protection from premature digestion by proteases secreted by the host cell. Subsequent to its synthesis, rCrFC is solubilized and purified under pyrogen-free conditions. Using established protocols, the protein can be denatured and renatured to recover its biological functionality. By manipulation of the 5' end of CrFC26, truncated constructs containing this cDNA are expressed by *S. cerevisiae* to give immunoreactive rCrFC. The rCrFC produced from both CrFC21 and CrFC26 constructs, solubilized by Triton X-100 or SDS, is found to be immunoreactive. Solubilized rCrFC was purified as a proenzyme and reversibly protected from activation by addition of $Me_2SO$.

8 Claims, 21 Drawing Sheets

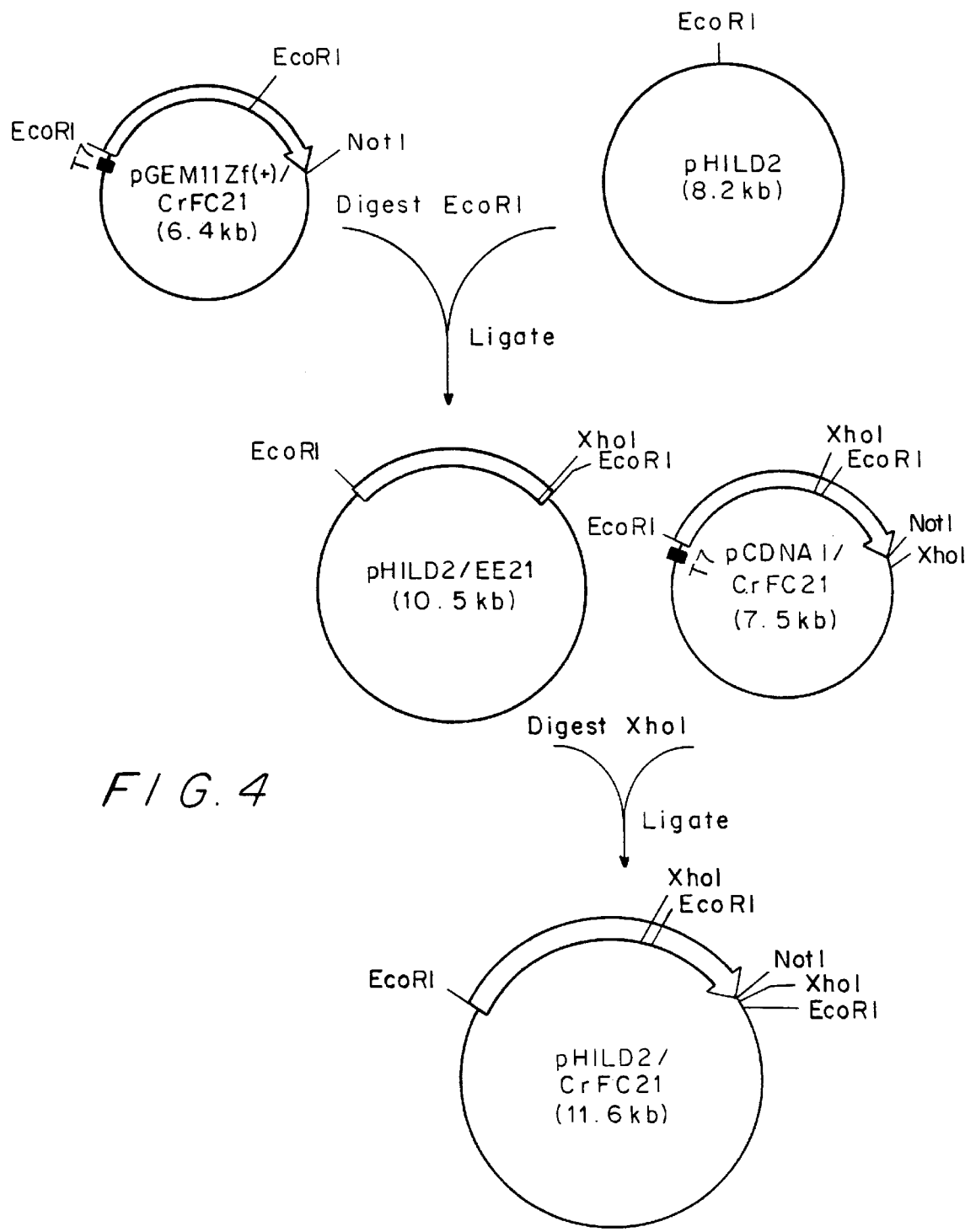
F I G. 4

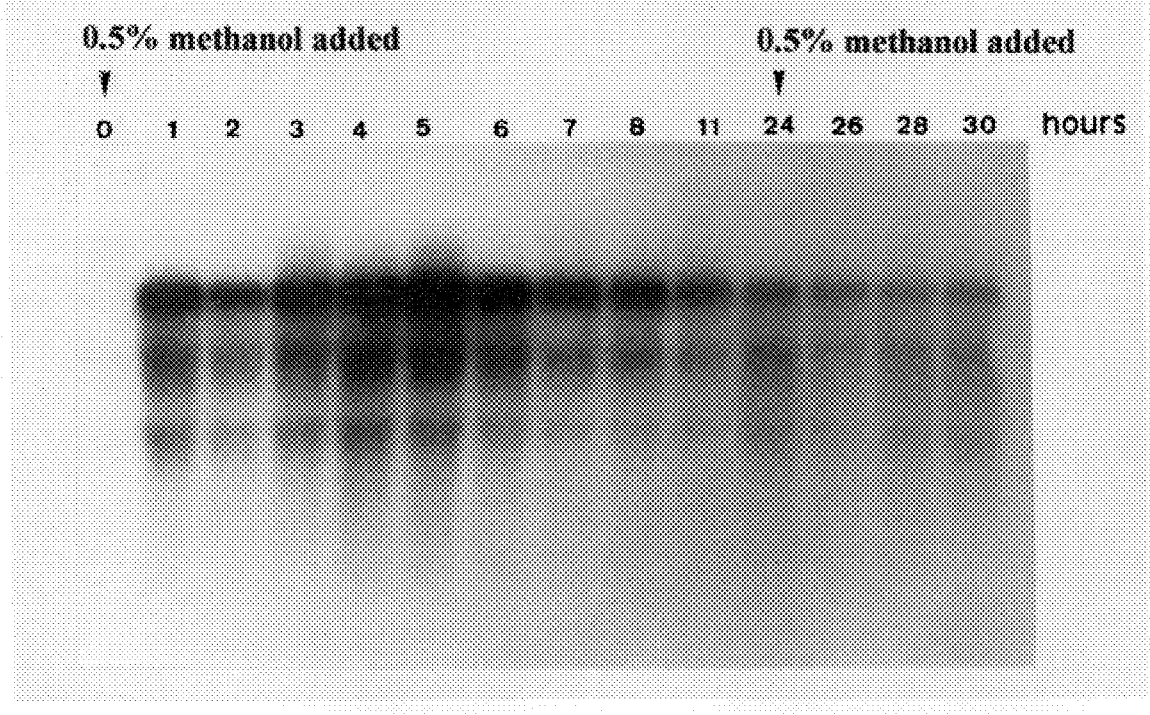

FIG. 11A

CrFC26 DELETION SUBCLONE 6a

YEpsecI — pGEM7/11zf(+) — CrFC26Δ6a

Gly Thr Arg Gly Ile Arg Ala Arg Arg Arg Met Pro Asp Lys Pro Glu Tyr
GGT ACC CGG GGG ATC CGG GCC CGA CGT CGC ATG CCT GAC AAG CCA GAG TAC
CCA TGG GCC CCC TAG GCC CGG GCT GCA GCG TAC GGA CTG TTC GGT CTC ATG
    SmaI         ApaI  AatII   SphI

CrFC26 DELETION SUBCLONE 9a

YEpsecI — pGEM7/11zf(+) — CrFC26Δ9a

Gly Thr Arg Gly Ile Arg Ala Arg Arg Arg Met Arg Pro Leu Leu Ser Pro
GGT ACC CGG GGG ATC CGG GCC CGA CGT CGC ATG CGG CCA TTA CTC TCT CCA
CCA TGG GCC CCC TAG GCC CGG GCT GCA GCG TAC GCC GGT AAT GAG AGA GGT
    SmaI         ApaI  AatII   SphI 1 2 3 4 5 6 7 8

1 2 3 4 5 6 7 8 9 10

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 4182 base pairs
      (B) TYPE: nucleic acid
      (C) STRANDEDNESS: single
      (D) TOPOLOGY: both (ii) MOLECULE TYPE: cDNA (iii) HYPOTHETICAL: NO (iv) ANTI-SENSE: NO (vi) ORIGINAL SOURCE:
      (A) ORGANISM: Carcinoscorpius rotundicauda (ix) FEATURE:
      (A) NAME/KEY: CDS
      (B) LOCATION: 569..3817

(xi) SEQUENCE DESCRIPTION: SEQ ID NO:1:

```
GTATTTAATG TCTCAACGGT AAAGGTTTCA TTGTAGCTAA TATTTAACTT CCTCCCTGTG        60

CCCCAAATCG CGAGTATGAC GTCAGTTAAG ACTTCGTATT TAAGAGTTA AACACGAGCC        120

TTAAAGAGCG ATATTTTTTT TGTTAAACAC TTCCAACTTA ATACAATTGG CAAACTTTCA       180

AAAATAAAGT GGAAAAGGAG GTAAAAAAGA TGAAAAAAAT TCGCATACAA TAGAATACAA       240

TAAAATGTGT TGTCTTTACT GTCAACACTT ACTGTTCGTT CGGTCACAGC TGTGAATCGG       300

GGTGACTTTA TGTTTGTAGT GGTCTTAAAA ACGGGTACTT GGTTGTTTTG AAAATTTTAA      360

AACCTACATA TGATTCTCCT AAAATTTTGT TTATAAATTA GCACCATTTG CGACCTAAAT     420

CTTTTTTGTA GTCTTAAGTT TAGTTGACAT AAAAACAAAA TTTGTAACAA CACACGGTAT     480

AAACTAAATA GCTTCAGATG GGTCGTATGA CAAGGAAACT TTTAAATAAT TATGAAAGTT     540

TTTTTAAAAT TTGACTAAGG TTTAGATT ATG TGG GTG ACA TGC TTC GAC ACG         592
                                 Met Trp Val Thr Cys Phe Asp Thr
                                   1               5

TTT CTT TTT GTT TGT GAA AGT TCA GTT TTC TGT TTG TTG TGT GTG TGG        640
Phe Leu Phe Val Cys Glu Ser Ser Val Phe Cys Leu Leu Cys Val Trp
    10                  15                  20

AGG TTT GGT TTC TGT AGG TGG CGT GTT TTC TAC AGT TTT CCA TTC GTT        688
Arg Phe Gly Phe Cys Arg Trp Arg Val Phe Tyr Ser Phe Pro Phe Val
25                  30                  35                  40

AAG TCA ACA GTT GTT TTA TTA CAG TGT TAC CAT TAC TCT CTC CAC AAT        736
Lys Ser Thr Val Val Leu Leu Gln Cys Tyr His Tyr Ser Leu His Asn
                45                  50                  55

ACC TCA AAG TTC TAC TCT GTG AAT CCT GAC AAG CCA GAG TAC ATT CTT        784
Thr Ser Lys Phe Tyr Ser Val Asn Pro Asp Lys Pro Glu Tyr Ile Leu
```

-continued

```
                   60                    65                     70
TCA GGT TTA GTT CTA GGG CTA CTA GCC CAA AAA ATG CGC CCA GTT CAG      832
Ser Gly Leu Val Leu Gly Leu Leu Ala Gln Lys Met Arg Pro Val Gln
         75                   80                    85

TCC AAA GGA GTA GAT CTA GGC TTG TGT GAT GAA ACG AGG TTC GAG TGT      880
Ser Lys Gly Val Asp Leu Gly Leu Cys Asp Glu Thr Arg Phe Glu Cys
         90                   95                   100

AAG TGT GGC GAT CCA GGC TAT GTG TTC AAC ATT CCA GTG AAA CAA TGT      928
Lys Cys Gly Asp Pro Gly Tyr Val Phe Asn Ile Pro Val Lys Gln Cys
105                  110                  115                  120

ACA TAC TTT TAT CGA TGG AGG CCG TAT TGT AAA CCA TGT GAT GAC CTG      976
Thr Tyr Phe Tyr Arg Trp Arg Pro Tyr Cys Lys Pro Cys Asp Asp Leu
                 125                  130                  135

GAG GCT AAG GAT ATT TGT CCA AAG TAC AAA CGA TGT CAA GAG TGT AAG     1024
Glu Ala Lys Asp Ile Cys Pro Lys Tyr Lys Arg Cys Gln Glu Cys Lys
             140                  145                  150

GCT GGT CTT GAT AGT TGT GTT ACT TGT CCA CCT AAC AAA TAT GGT ACT     1072
Ala Gly Leu Asp Ser Cys Val Thr Cys Pro Pro Asn Lys Tyr Gly Thr
             155                  160                  165

TGG TGT AGC GGT GAA TGT CAG TGT AAG AAT GGA GGT ATC TGT GAC CAG     1120
Trp Cys Ser Gly Glu Cys Gln Cys Lys Asn Gly Gly Ile Cys Asp Gln
         170                  175                  180

AGG ACA GGA GCT TGT GCA TGT CGT GAC AGA TAT GAA GGG GTG CAC TGT     1168
Arg Thr Gly Ala Cys Ala Cys Arg Asp Arg Tyr Glu Gly Val His Cys
185                  190                  195                  200

GAA ATT CTC AAA GGT TGT CCT CTT CTT CCA TCG GAT TCT CAG GTT CAG     1216
Glu Ile Leu Lys Gly Cys Pro Leu Leu Pro Ser Asp Ser Gln Val Gln
                 205                  210                  215

GAA GTC AGA AAT CCA CCA GAT AAT CCC CAA ACT ATT GAC TAC AGC TGT     1264
Glu Val Arg Asn Pro Pro Asp Asn Pro Gln Thr Ile Asp Tyr Ser Cys
             220                  225                  230

TCA CCA GGG TTC AAG CTT AAG GGT ATG GCA CGA ATT AGC TGT CTC CCA     1312
Ser Pro Gly Phe Lys Leu Lys Gly Met Ala Arg Ile Ser Cys Leu Pro
             235                  240                  245

AAT GGA CAG TGG AGT AAC TTT CCA CCC AAA TGT ATT CGA GAA TGT GCC     1360
Asn Gly Gln Trp Ser Asn Phe Pro Pro Lys Cys Ile Arg Glu Cys Ala
         250                  255                  260

ATG GTT TCA TCT CCA GAA CAT GGG AAA GTG AAT GCT CTT AGT GGT GAT     1408
Met Val Ser Ser Pro Glu His Gly Lys Val Asn Ala Leu Ser Gly Asp
265                  270                  275                  280

ATG ATA GAA GGG GCT ACT TTA CGG TTC TCA TGT GAT AGT CCC TAC TAC     1456
Met Ile Glu Gly Ala Thr Leu Arg Phe Ser Cys Asp Ser Pro Tyr Tyr
                 285                  290                  295

TTG ATT GGT CAA GAA ACA TTA ACC TGT CAG GGT AAT GGT CAG TGG AAT     1504
Leu Ile Gly Gln Glu Thr Leu Thr Cys Gln Gly Asn Gly Gln Trp Asn
             300                  305                  310

GGA CAG ATA CCA CAA TGT AAG AAC TTA GTC TTC TGT CCT GAC CTG GAT     1552
Gly Gln Ile Pro Gln Cys Lys Asn Leu Val Phe Cys Pro Asp Leu Asp
             315                  320                  325

CCT GTA AAC CAT GCT GAA CAC AAG GTT AAA ATT GGT GTG GAA CAA AAA     1600
Pro Val Asn His Ala Glu His Lys Val Lys Ile Gly Val Glu Gln Lys
         330                  335                  340

TAT GGT CAG TTT CCT CAA GGC ACT GAA GTG ACC TAT ACG TGT TCG GGT     1648
Tyr Gly Gln Phe Pro Gln Gly Thr Glu Val Thr Tyr Thr Cys Ser Gly
345                  350                  355                  360

AAC TAC TTC TTG ATG GGT TTT GAC ACC TTA AAA TGT AAC CCT GAT GGG     1696
Asn Tyr Phe Leu Met Gly Phe Asp Thr Leu Lys Cys Asn Pro Asp Gly
                 365                  370                  375

TCT TGG TCA GGA TCA CAG CCA TCC TGT GTT AAA GTG GCA GAC AGA GAG     1744
Ser Trp Ser Gly Ser Gln Pro Ser Cys Val Lys Val Ala Asp Arg Glu
```

-continued

```
                      380                       385                       390
GTC GAC TGT GAC AGT AAA GCT GTA GAC TTC TTG GAT GAT GTT GGT GAA        1792
Val Asp Cys Asp Ser Lys Ala Val Asp Phe Leu Asp Asp Val Gly Glu
            395                     400                     405

CCT GTC AGG ATC CAC TGT CCT GCT GGC TGT TCT TTG ACA GCT GGT ACT        1840
Pro Val Arg Ile His Cys Pro Ala Gly Cys Ser Leu Thr Ala Gly Thr
            410                     415                     420

GTG TGG GGT ACA GCC ATA TAC CAT GAA CTT TCC TCA GTG TGT CGT GCA        1888
Val Trp Gly Thr Ala Ile Tyr His Glu Leu Ser Ser Val Cys Arg Ala
425                     430                     435                     440

GCC ATC CAT GCT GGC AAG CTT CCA AAC TCT GGA GGA GCG GTG CAT GTT        1936
Ala Ile His Ala Gly Lys Leu Pro Asn Ser Gly Gly Ala Val His Val
            445                     450                     455

GTG AAC AAT GGC CCC TAC TCG GAC TTT CTG GGT AGT GAC CTG AAT GGG        1984
Val Asn Asn Gly Pro Tyr Ser Asp Phe Leu Gly Ser Asp Leu Asn Gly
            460                     465                     470

ATA AAA TCC GAA GAG TTG AAG TCT CTT GCC CGG AGT TTC CGA TTC GAT        2032
Ile Lys Ser Glu Glu Leu Lys Ser Leu Ala Arg Ser Phe Arg Phe Asp
            475                     480                     485

TAT GTC AGT TCC TCC ACA GCA GGT AAA TCA GGA TGT CCT GAT GGA TGG        2080
Tyr Val Ser Ser Ser Thr Ala Gly Lys Ser Gly Cys Pro Asp Gly Trp
            490                     495                     500

TTT GAG GTA GAC GAG AAC TGT GTG TAC GTT ACA TCA AAA CAG AGA GCC        2128
Phe Glu Val Asp Glu Asn Cys Val Tyr Val Thr Ser Lys Gln Arg Ala
505                     510                     515                     520

TGG GAA AGA GCT CAA GGT GTG TGT ACC AAT ATG GCT GCT CGT CTT GCT        2176
Trp Glu Arg Ala Gln Gly Val Cys Thr Asn Met Ala Ala Arg Leu Ala
            525                     530                     535

GTG CTG GAC AAA GAT GTA ATT CCA AAT TCA TTG ACT GAG ACT CTA CGA        2224
Val Leu Asp Lys Asp Val Ile Pro Asn Ser Leu Thr Glu Thr Leu Arg
            540                     545                     550

GGG AAA GGG TTA ACA ACC ACG TGG ATA GGA TTG CAC AGA CTA GAT GCT        2272
Gly Lys Gly Leu Thr Thr Thr Trp Ile Gly Leu His Arg Leu Asp Ala
            555                     560                     565

GAG AAG CCC TTT ATT TGG GAG TTA ATG GAT CGT AGT AAT GTG GTT CTG        2320
Glu Lys Pro Phe Ile Trp Glu Leu Met Asp Arg Ser Asn Val Val Leu
            570                     575                     580

AAT GAT AAC CTA ACA TTC TGG GCC TCT GGC GAA CCT GGA AAT GAA ACT        2368
Asn Asp Asn Leu Thr Phe Trp Ala Ser Gly Glu Pro Gly Asn Glu Thr
585                     590                     595                     600

AAC TGT GTA TAT ATG GAC ATC CAA GAT CAG TTG CAG TCT GTG TGG AAA        2416
Asn Cys Val Tyr Met Asp Ile Gln Asp Gln Leu Gln Ser Val Trp Lys
            605                     610                     615

ACC AAG TCA TGT TTT CAG CCC TCA AGT TTT GCT TGC ATG ATG GAT CTG        2464
Thr Lys Ser Cys Phe Gln Pro Ser Ser Phe Ala Cys Met Met Asp Leu
            620                     625                     630

TCA GAC AGA AAT AAA GCC AAA TGC GAT GAT CCT GGA TCA CTG GAA AAT        2512
Ser Asp Arg Asn Lys Ala Lys Cys Asp Asp Pro Gly Ser Leu Glu Asn
            635                     640                     645

GGA CAC GCC ACA CTT CAT GGA CAA AGT ATT GAT GGG TTC TAT GCT GGT        2560
Gly His Ala Thr Leu His Gly Gln Ser Ile Asp Gly Phe Tyr Ala Gly
            650                     655                     660

TCT TCT ATA AGG TAC AGC TGT GAG GTT CTC CAC TAC CTC AGT GGA ACT        2608
Ser Ser Ile Arg Tyr Ser Cys Glu Val Leu His Tyr Leu Ser Gly Thr
665                     670                     675                     680

GAA ACC GTA ACT TGT ACA ACA AAT GGC ACA TGG AGT GCT CCT AAA CCT        2656
Glu Thr Val Thr Cys Thr Thr Asn Gly Thr Trp Ser Ala Pro Lys Pro
            685                     690                     695

CGA TGT ATC AAA GTC ATC ACC TGC CAA AAC CCC CCT GTA CCA TCA TAT        2704
Arg Cys Ile Lys Val Ile Thr Cys Gln Asn Pro Pro Val Pro Ser Tyr
```

-continued

```
                        700                   705                   710
GGT TCT GTG GAA ATC AAA CCC CCA AGT CGG ACA AAC TCG ATA AGT CGT              2752
Gly Ser Val Glu Ile Lys Pro Pro Ser Arg Thr Asn Ser Ile Ser Arg
            715                   720                   725

GTT GGG TCA CCT TTC TTG AGG TTG CCA CGG TTA CCC CTC CCA TTA GCC              2800
Val Gly Ser Pro Phe Leu Arg Leu Pro Arg Leu Pro Leu Pro Leu Ala
        730                   735                   740

AGA GCA GCC AAA CCT CCT CCA AAA CCT AGA TCC TCA CAA CCC TCT ACT              2848
Arg Ala Ala Lys Pro Pro Pro Lys Pro Arg Ser Ser Gln Pro Ser Thr
745                   750                   755                   760

GTG GAC TTG GCT TCT AAA GTT AAA CTA CCT GAA GGT CAT TAC CGG GTA              2896
Val Asp Leu Ala Ser Lys Val Lys Leu Pro Glu Gly His Tyr Arg Val
                765                   770                   775

GGG TCT CGA GCC ATT TAC ACG TGC GAG TCG AGA TAC TAC GAA CTA CTT              2944
Gly Ser Arg Ala Ile Tyr Thr Cys Glu Ser Arg Tyr Tyr Glu Leu Leu
            780                   785                   790

GGA TCT CAA GGC AGA AGA TGT GAC TCT AAT GGA AAC TGG AGT GGT CGG              2992
Gly Ser Gln Gly Arg Arg Cys Asp Ser Asn Gly Asn Trp Ser Gly Arg
        795                   800                   805

CCA GCG AGC TGT ATT CCA GTT TGT GGA CGG TCA GAC TCT CCT CGT TCT              3040
Pro Ala Ser Cys Ile Pro Val Cys Gly Arg Ser Asp Ser Pro Arg Ser
810                   815                   820

CCT TTT ATC TGG AAT GGG AAT TCT ACA GAA ATA GGT CAG TGG CCG TGG              3088
Pro Phe Ile Trp Asn Gly Asn Ser Thr Glu Ile Gly Gln Trp Pro Trp
825                   830                   835                   840

CAG GCA GGA ATC TCT AGA TGG CTT GCA GAC CAC AAT ATG TGG TTT CTC              3136
Gln Ala Gly Ile Ser Arg Trp Leu Ala Asp His Asn Met Trp Phe Leu
                845                   850                   855

CAG TGT GGA GGA TCT CTA TTG AAT GAG AAA TGG ATC GTC ACT GCT GCC              3184
Gln Cys Gly Gly Ser Leu Leu Asn Glu Lys Trp Ile Val Thr Ala Ala
            860                   865                   870

CAC TGT GTC ACC TAC TCT GCT ACT GCT GAG ATT ATT GAC CCC AAT CAG              3232
His Cys Val Thr Tyr Ser Ala Thr Ala Glu Ile Ile Asp Pro Asn Gln
        875                   880                   885

TTT AAA ATG TAT CTG GGC AAG TAC TAC CGT GAT GAC AGT AGA GAC GAT              3280
Phe Lys Met Tyr Leu Gly Lys Tyr Tyr Arg Asp Asp Ser Arg Asp Asp
    890                   895                   900

GAC TAT GTA CAA GTA AGA GAG GCT CTT GAG ATC CAC GTG AAT CCT AAC              3328
Asp Tyr Val Gln Val Arg Glu Ala Leu Glu Ile His Val Asn Pro Asn
905                   910                   915                   920

TAC GAC CCC GGC AAT CTC AAC TTT GAC ATA GCC CTA ATT CAA CTG AAA              3376
Tyr Asp Pro Gly Asn Leu Asn Phe Asp Ile Ala Leu Ile Gln Leu Lys
                925                   930                   935

ACT CCT GTT ACT TTG ACA ACA CGA GTC CAA CCA ATC TGT CTG CCT ACT              3424
Thr Pro Val Thr Leu Thr Thr Arg Val Gln Pro Ile Cys Leu Pro Thr
            940                   945                   950

GAC ATC ACA ACA AGA GAA CAC TTG AAG GAG GGA ACA TTA GCA GTG GTG              3472
Asp Ile Thr Thr Arg Glu His Leu Lys Glu Gly Thr Leu Ala Val Val
        955                   960                   965

ACA GGT TGG GGT TTG AAT GAA AAC AAC ACC TAT TCA GAG ACG ATT CAA              3520
Thr Gly Trp Gly Leu Asn Glu Asn Asn Thr Tyr Ser Glu Thr Ile Gln
    970                   975                   980

CAA GCT GTG CTA CCT GTT GTT GCA GCC AGC ACC TGT GAA GAG GGG TAC              3568
Gln Ala Val Leu Pro Val Val Ala Ala Ser Thr Cys Glu Glu Gly Tyr
985                   990                   995                   1000

AAG GAA GCA GAC TTA CCA CTG ACA GTA ACA GAG AAC ATG TTC TGT GCA              3616
Lys Glu Ala Asp Leu Pro Leu Thr Val Thr Glu Asn Met Phe Cys Ala
                1005                  1010                  1015

GGT TAC AAG AAG GGA CGT TAT GAT GCC TGC AGT GGG GAC AGT GGA GGA              3664
Gly Tyr Lys Lys Gly Arg Tyr Asp Ala Cys Ser Gly Asp Ser Gly Gly
```

```
                     1020                1025                1030
CCT TTA GTG TTT GCT GAT GAT TCC CGT ACC GAA AGG CGG TGG GTC TTG      3712
Pro Leu Val Phe Ala Asp Asp Ser Arg Thr Glu Arg Arg Trp Val Leu
        1035                1040                1045

GAA GGG ATT GTC AGC TGG GGC AGT CCC AGT GGA TGT GGC AAG GCG AAC      3760
Glu Gly Ile Val Ser Trp Gly Ser Pro Ser Gly Cys Gly Lys Ala Asn
    1050                1055                1060

CAG TAC GGG GGC TTC ACT AAA GTT AAC GTT TTC CTG TCA TGG ATT AGG      3808
Gln Tyr Gly Gly Phe Thr Lys Val Asn Val Phe Leu Ser Trp Ile Arg
1065                1070                1075                1080

CAG TTC ATT TGAAACTGAT CTAAATATTT TAAGCATGGT TATAAACGTC              3857
Gln Phe Ile

TTGTTCCTAT TATTGCTTTA CTGGTTTAAC CCATAAGAAG GTTAACGGGG TAAGGCACAA    3917

GGATCATTGT TTCTGTTTGT TTTTACAAAT GGTTCTTTTA GTCAGTGAAT GAGAATAGTA    3977

TCCATTGGAG ACTGTTACCT TTTATTCTAC CTTTTTATAT TACTATGCAA GTATTTGGGA    4037

TATCTTCTAC ACATGAAAAT TCTGTCATTT TACCATAAAT TTGGTTTCTG GTGTGTGTGT    4097

TAAGTCCACC ACTAGAGAAC GATGTAATTT TCAATAGTAC ATGAAATAAA TATAGAACAA    4157

ATCTATTATA AAAAAAAAAA AAAAA                                          4182

(2) INFORMATION FOR SEQ ID NO:2:

(i) SEQUENCE CHARACTERISTICS:
        (A) LENGTH: 1083 amino acids
        (B) TYPE: amino acid
        (D) TOPOLOGY: linear (ii) MOLECULE TYPE: protein (xi) SEQUENCE DESCRIPTION: SEQ ID NO:2:

Met Trp Val Thr Cys Phe Asp Thr Phe Leu Phe Val Cys Glu Ser Ser
 1               5                  10                  15

Val Phe Cys Leu Leu Cys Val Trp Arg Phe Gly Phe Cys Arg Trp Arg
            20                  25                  30

Val Phe Tyr Ser Phe Pro Phe Val Lys Ser Thr Val Val Leu Leu Gln
        35                  40                  45

Cys Tyr His Tyr Ser Leu His Asn Thr Ser Lys Phe Tyr Ser Val Asn
    50                  55                  60

Pro Asp Lys Pro Glu Tyr Ile Leu Ser Gly Leu Val Leu Gly Leu Leu
65                  70                  75                  80

Ala Gln Lys Met Arg Pro Val Gln Ser Lys Gly Val Asp Leu Gly Leu
                85                  90                  95

Cys Asp Glu Thr Arg Phe Glu Cys Lys Cys Gly Asp Pro Gly Tyr Val
            100                 105                 110

Phe Asn Ile Pro Val Lys Gln Cys Thr Tyr Phe Tyr Arg Trp Arg Pro
        115                 120                 125

Tyr Cys Lys Pro Cys Asp Asp Leu Glu Ala Lys Asp Ile Cys Pro Lys
    130                 135                 140

Tyr Lys Arg Cys Gln Glu Cys Lys Ala Gly Leu Asp Ser Cys Val Thr
145                 150                 155                 160

Cys Pro Pro Asn Lys Tyr Gly Thr Trp Cys Ser Gly Glu Cys Gln Cys
                165                 170                 175

Lys Asn Gly Gly Ile Cys Asp Gln Arg Thr Gly Ala Cys Ala Cys Arg
            180                 185                 190

Asp Arg Tyr Glu Gly Val His Cys Glu Ile Leu Lys Gly Cys Pro Leu
        195                 200                 205
```

```
Leu Pro Ser Asp Ser Gln Val Gln Glu Val Arg Asn Pro Pro Asp Asn
    210                 215                 220

Pro Gln Thr Ile Asp Tyr Ser Cys Ser Pro Gly Phe Lys Leu Lys Gly
225                 230                 235                 240

Met Ala Arg Ile Ser Cys Leu Pro Asn Gly Gln Trp Ser Asn Phe Pro
                245                 250                 255

Pro Lys Cys Ile Arg Glu Cys Ala Met Val Ser Ser Pro Glu His Gly
            260                 265                 270

Lys Val Asn Ala Leu Ser Gly Asp Met Ile Glu Gly Ala Thr Leu Arg
        275                 280                 285

Phe Ser Cys Asp Ser Pro Tyr Tyr Leu Ile Gly Gln Glu Thr Leu Thr
    290                 295                 300

Cys Gln Gly Asn Gly Gln Trp Asn Gly Gln Ile Pro Gln Cys Lys Asn
305                 310                 315                 320

Leu Val Phe Cys Pro Asp Leu Asp Pro Val Asn His Ala Glu His Lys
                325                 330                 335

Val Lys Ile Gly Val Glu Gln Lys Tyr Gly Gln Phe Pro Gln Gly Thr
            340                 345                 350

Glu Val Thr Tyr Thr Cys Ser Gly Asn Tyr Phe Leu Met Gly Phe Asp
        355                 360                 365

Thr Leu Lys Cys Asn Pro Asp Gly Ser Trp Ser Gly Ser Gln Pro Ser
    370                 375                 380

Cys Val Lys Val Ala Asp Arg Glu Val Asp Cys Asp Ser Lys Ala Val
385                 390                 395                 400

Asp Phe Leu Asp Asp Val Gly Glu Pro Val Arg Ile His Cys Pro Ala
                405                 410                 415

Gly Cys Ser Leu Thr Ala Gly Thr Val Trp Gly Thr Ala Ile Tyr His
            420                 425                 430

Glu Leu Ser Ser Val Cys Arg Ala Ala Ile His Ala Gly Lys Leu Pro
        435                 440                 445

Asn Ser Gly Gly Ala Val His Val Val Asn Asn Gly Pro Tyr Ser Asp
450                 455                 460

Phe Leu Gly Ser Asp Leu Asn Gly Ile Lys Ser Glu Glu Leu Lys Ser
465                 470                 475                 480

Leu Ala Arg Ser Phe Arg Phe Asp Tyr Val Ser Ser Ser Thr Ala Gly
                485                 490                 495

Lys Ser Gly Cys Pro Asp Gly Trp Phe Glu Val Asp Glu Asn Cys Val
            500                 505                 510

Tyr Val Thr Ser Lys Gln Arg Ala Trp Glu Arg Ala Gln Gly Val Cys
        515                 520                 525

Thr Asn Met Ala Ala Arg Leu Ala Val Leu Asp Lys Asp Val Ile Pro
    530                 535                 540

Asn Ser Leu Thr Glu Thr Leu Arg Gly Lys Gly Leu Thr Thr Thr Trp
545                 550                 555                 560

Ile Gly Leu His Arg Leu Asp Ala Glu Lys Pro Phe Ile Trp Glu Leu
                565                 570                 575

Met Asp Arg Ser Asn Val Val Leu Asn Asp Asn Leu Thr Phe Trp Ala
            580                 585                 590

Ser Gly Glu Pro Gly Asn Glu Thr Asn Cys Val Tyr Met Asp Ile Gln
        595                 600                 605

Asp Gln Leu Gln Ser Val Trp Lys Thr Lys Ser Cys Phe Gln Pro Ser
    610                 615                 620

Ser Phe Ala Cys Met Met Asp Leu Ser Asp Arg Asn Lys Ala Lys Cys
625                 630                 635                 640
```

```
Asp Asp Pro Gly Ser Leu Glu Asn Gly His Ala Thr Leu His Gly Gln
            645                 650                 655

Ser Ile Asp Gly Phe Tyr Ala Gly Ser Ser Ile Arg Tyr Ser Cys Glu
            660                 665                 670

Val Leu His Tyr Leu Ser Gly Thr Glu Thr Val Thr Cys Thr Thr Asn
            675                 680                 685

Gly Thr Trp Ser Ala Pro Lys Pro Arg Cys Ile Lys Val Ile Thr Cys
690                     695                 700

Gln Asn Pro Pro Val Pro Ser Tyr Gly Ser Val Glu Ile Lys Pro Pro
705                     710                 715                 720

Ser Arg Thr Asn Ser Ile Ser Arg Val Gly Ser Pro Phe Leu Arg Leu
            725                 730                 735

Pro Arg Leu Pro Leu Pro Leu Ala Arg Ala Ala Lys Pro Pro Pro Lys
            740                 745                 750

Pro Arg Ser Ser Gln Pro Ser Thr Val Asp Leu Ala Ser Lys Val Lys
            755                 760                 765

Leu Pro Glu Gly His Tyr Arg Val Gly Ser Arg Ala Ile Tyr Thr Cys
            770                 775                 780

Glu Ser Arg Tyr Tyr Glu Leu Leu Gly Ser Gln Gly Arg Arg Cys Asp
785                     790                 795                 800

Ser Asn Gly Asn Trp Ser Gly Arg Pro Ala Ser Cys Ile Pro Val Cys
            805                 810                 815

Gly Arg Ser Asp Ser Pro Arg Ser Pro Phe Ile Trp Asn Gly Asn Ser
            820                 825                 830

Thr Glu Ile Gly Gln Trp Pro Trp Gln Ala Gly Ile Ser Arg Trp Leu
            835                 840                 845

Ala Asp His Asn Met Trp Phe Leu Gln Cys Gly Gly Ser Leu Leu Asn
850                     855                 860

Glu Lys Trp Ile Val Thr Ala Ala His Cys Val Thr Tyr Ser Ala Thr
865                     870                 875                 880

Ala Glu Ile Ile Asp Pro Asn Gln Phe Lys Met Tyr Leu Gly Lys Tyr
            885                 890                 895

Tyr Arg Asp Asp Ser Arg Asp Asp Tyr Val Gln Val Arg Glu Ala
            900                 905                 910

Leu Glu Ile His Val Asn Pro Asn Tyr Asp Pro Gly Asn Leu Asn Phe
            915                 920                 925

Asp Ile Ala Leu Ile Gln Leu Lys Thr Pro Val Thr Leu Thr Thr Arg
930                     935                 940

Val Gln Pro Ile Cys Leu Pro Thr Asp Ile Thr Thr Arg Glu His Leu
945                     950                 955                 960

Lys Glu Gly Thr Leu Ala Val Val Thr Gly Trp Gly Leu Asn Glu Asn
            965                 970                 975

Asn Thr Tyr Ser Glu Thr Ile Gln Gln Ala Val Leu Pro Val Val Ala
            980                 985                 990

Ala Ser Thr Cys Glu Glu Gly Tyr Lys Glu Ala Asp Leu Pro Leu Thr
            995                 1000                1005

Val Thr Glu Asn Met Phe Cys Ala Gly Tyr Lys Lys Gly Arg Tyr Asp
    1010                1015                1020

Ala Cys Ser Gly Asp Ser Gly Gly Pro Leu Val Phe Ala Asp Asp Ser
1025                    1030                1035                1040

Arg Thr Glu Arg Arg Trp Val Leu Glu Gly Ile Val Ser Trp Gly Ser
            1045                1050                1055

Pro Ser Gly Cys Gly Lys Ala Asn Gln Tyr Gly Gly Phe Thr Lys Val
```

```
                    1060              1065              1070
Asn Val Phe Leu Ser Trp Ile Arg Gln Phe Ile
                1075              1080

(2) INFORMATION FOR SEQ ID NO:3:

(i) SEQUENCE CHARACTERISTICS:
        (A) LENGTH: 3448 base pairs
        (B) TYPE: nucleic acid
        (C) STRANDEDNESS: single
        (D) TOPOLOGY: both (ii) MOLECULE TYPE: cDNA (iii) HYPOTHETICAL: NO (iv) ANTI-SENSE: NO (vi) ORIGINAL SOURCE:
        (A) ORGANISM: Carcinoscorpius rotundicauda (ix) FEATURE:
        (A) NAME/KEY: CDS
        (B) LOCATION: 18..3074

(xi) SEQUENCE DESCRIPTION: SEQ ID NO:3:

GTGAAGGTAA CTTAAGT ATG GTC TTA GCG TCG TTT TTG GTG TCT GGT TTA            50
                   Met Val Leu Ala Ser Phe Leu Val Ser Gly Leu
                     1               5                      10

GTT CTA GGG CTA CTA GCC CAA AAA ATG CGC CCA GTT CAG TCC AAA GGA           98
Val Leu Gly Leu Leu Ala Gln Lys Met Arg Pro Val Gln Ser Lys Gly
             15                  20                  25

GTA GAT CTA GGC TTG TGT GAT GAA ACG AGG TTC GAG TGT AAG TGT GGC          146
Val Asp Leu Gly Leu Cys Asp Glu Thr Arg Phe Glu Cys Lys Cys Gly
         30                  35                  40

GAT CCA GGC TAT GTG TTC AAC ATT CCA GTG AAA CAA TGT ACA TAC TTT          194
Asp Pro Gly Tyr Val Phe Asn Ile Pro Val Lys Gln Cys Thr Tyr Phe
     45                  50                  55

TAT CGA TGG AGG CCG TAT TGT AAA CCA TGT GAT GAC CTG GAG GCT AAG          242
Tyr Arg Trp Arg Pro Tyr Cys Lys Pro Cys Asp Asp Leu Glu Ala Lys
 60                  65                  70                  75

GAT ATT TGT CCA AAG TAC AAA CGA TGT CAA GAG TGT AAG GCT GGT CTT          290
Asp Ile Cys Pro Lys Tyr Lys Arg Cys Gln Glu Cys Lys Ala Gly Leu
                 80                  85                  90

GAT AGT TGT GTT ACT TGT CCA CCT AAC AAA TAT GGT ACT TGG TGT AGC          338
Asp Ser Cys Val Thr Cys Pro Pro Asn Lys Tyr Gly Thr Trp Cys Ser
             95                 100                 105

GGT GAA TGT CAG TGT AAG AAT GGA GGT ATC TGT GAC CAG AGG ACA GGA          386
Gly Glu Cys Gln Cys Lys Asn Gly Gly Ile Cys Asp Gln Arg Thr Gly
         110                 115                 120

GCT TGT GCA TGT CGT GAC AGA TAT GAA GGG GTG CAC TGT GAA ATT CTC          434
Ala Cys Ala Cys Arg Asp Arg Tyr Glu Gly Val His Cys Glu Ile Leu
     125                 130                 135

AAA GGT TGT CCT CTT CTT CCA TCG GAT TCT CAG GTT CAG GAA GTC AGA          482
Lys Gly Cys Pro Leu Leu Pro Ser Asp Ser Gln Val Gln Glu Val Arg
140                 145                 150                 155

AAT CCA CCA GAT AAT CCC CAA ACT ATT GAC TAC AGC TGT TCA CCA GGG          530
Asn Pro Pro Asp Asn Pro Gln Thr Ile Asp Tyr Ser Cys Ser Pro Gly
                160                 165                 170

TTC AAG CTT AAG GGT ATG GCA CGA ATT AGC TGT CTC CCA AAT GGA CAG          578
Phe Lys Leu Lys Gly Met Ala Arg Ile Ser Cys Leu Pro Asn Gly Gln
            175                 180                 185

TGG AGT AAC TTT CCA CCC AAA TGT ATT CGA GAA TGT GCC ATG GTT TCA          626
Trp Ser Asn Phe Pro Pro Lys Cys Ile Arg Glu Cys Ala Met Val Ser
        190                 195                 200
```

-continued

| | |
|---|---|
| TCT CCA GAA CAT GGG AAA GTG AAT GCT CTT AGT GGT GAT ATG ATA GAA<br>Ser Pro Glu His Gly Lys Val Asn Ala Leu Ser Gly Asp Met Ile Glu<br>205              210                   215 | 674 |
| GGG GCT ACT TTA CGG TTC TCA TGT GAT AGT CCC TAC TAC TTG ATT GGT<br>Gly Ala Thr Leu Arg Phe Ser Cys Asp Ser Pro Tyr Tyr Leu Ile Gly<br>220              225                   230                   235 | 722 |
| CAA GAA ACA TTA ACC TGT CAG GGT AAT GGT CAG TGG AAT GGA CAG ATA<br>Gln Glu Thr Leu Thr Cys Gln Gly Asn Gly Gln Trp Asn Gly Gln Ile<br>                   240                   245                   250 | 770 |
| CCA CAA TGT AAG AAC TTG GTC TTC TGT CCT GAC CTG GAT CCT GTA AAC<br>Pro Gln Cys Lys Asn Leu Val Phe Cys Pro Asp Leu Asp Pro Val Asn<br>          255                   260                   265 | 818 |
| CAT GCT GAA CAC AAG GTT AAA ATT GGT GTG GAA CAA AAA TAT GGT CAG<br>His Ala Glu His Lys Val Lys Ile Gly Val Glu Gln Lys Tyr Gly Gln<br>          270                   275                   280 | 866 |
| TTT CCT CAA GGC ACT GAA GTG ACC TAT ACG TGT TCG GGT AAC TAC TTC<br>Phe Pro Gln Gly Thr Glu Val Thr Tyr Thr Cys Ser Gly Asn Tyr Phe<br>285                   290                   295 | 914 |
| TTG ATG GGT TTT GAC ACC TTA AAA TGT AAC CCT GAT GGG TCT TGG TCA<br>Leu Met Gly Phe Asp Thr Leu Lys Cys Asn Pro Asp Gly Ser Trp Ser<br>300                   305                   310                   315 | 962 |
| GGA TCA CAG CCA TCC TGT GTT AAA GTG GCA GAC AGA GAG GTC GAC TGT<br>Gly Ser Gln Pro Ser Cys Val Lys Val Ala Asp Arg Glu Val Asp Cys<br>                   320                   325                   330 | 1010 |
| GAC AGT AAA GCT GTA GAC TTC TTG GAT GAT GTT GGT GAA CCT GTC AGG<br>Asp Ser Lys Ala Val Asp Phe Leu Asp Asp Val Gly Glu Pro Val Arg<br>          335                   340                   345 | 1058 |
| ATC CAC TGT CCT GCT GGC TGT TCT TTG ACA GCT GGT ACT GTG TGG GGT<br>Ile His Cys Pro Ala Gly Cys Ser Leu Thr Ala Gly Thr Val Trp Gly<br>          350                   355                   360 | 1106 |
| ACA GCC ATA TAC CAT GAA CTT TCC TCA GTG TGT CGT GCA GCC ATC CAT<br>Thr Ala Ile Tyr His Glu Leu Ser Ser Val Cys Arg Ala Ala Ile His<br>365                   370                   375 | 1154 |
| GCT GGC AAG CTT CCA AAC TCT GGA GGA GCG GTG CAT GTT GTG AAC AAT<br>Ala Gly Lys Leu Pro Asn Ser Gly Gly Ala Val His Val Val Asn Asn<br>380                   385                   390                   395 | 1202 |
| GGC CCC TAC TCG GAC TTT CTG GGT AGT GAC CTG AAT GGG ATA AAA TCG<br>Gly Pro Tyr Ser Asp Phe Leu Gly Ser Asp Leu Asn Gly Ile Lys Ser<br>                   400                   405                   410 | 1250 |
| GAA GAG TTG AAG TCT CTT GCC CGG AGT TTC CGA TTC GAT TAT GTC CGT<br>Glu Glu Leu Lys Ser Leu Ala Arg Ser Phe Arg Phe Asp Tyr Val Arg<br>          415                   420                   425 | 1298 |
| TCC TCC ACA GCA GGT AAA TCA GGA TGT CCT GAT GGA TGG TTT GAG GTA<br>Ser Ser Thr Ala Gly Lys Ser Gly Cys Pro Asp Gly Trp Phe Glu Val<br>          430                   435                   440 | 1346 |
| GAC GAG AAC TGT GTG TAC GTT ACA TCA AAA CAG AGA GCC TGG GAA AGA<br>Asp Glu Asn Cys Val Tyr Val Thr Ser Lys Gln Arg Ala Trp Glu Arg<br>445                   450                   455 | 1394 |
| GCT CAA GGT GTG TGT ACC AAT ATG GCT GCT CGT CTT GCT GTG CTG GAC<br>Ala Gln Gly Val Cys Thr Asn Met Ala Ala Arg Leu Ala Val Leu Asp<br>460                   465                   470                   475 | 1442 |
| AAA GAT GTA ATT CCA AAT TCG TTG ACT GAG ACT CTA CGA GGG AAA GGG<br>Lys Asp Val Ile Pro Asn Ser Leu Thr Glu Thr Leu Arg Gly Lys Gly<br>                   480                   485                   490 | 1490 |
| TTA ACA ACC ACG TGG ATA GGA TTG CAC AGA CTA GAT GCT GAG AAG CCC<br>Leu Thr Thr Thr Trp Ile Gly Leu His Arg Leu Asp Ala Glu Lys Pro<br>          495                   500                   505 | 1538 |
| TTT ATT TGG GAG TTA ATG GAT CGT AGT AAT GTG GTT CTG AAT GAT AAC<br>Phe Ile Trp Glu Leu Met Asp Arg Ser Asn Val Val Leu Asn Asp Asn<br>          510                   515                   520 | 1586 |

-continued

```
CTA ACA TTC TGG GCC TCT GGC GAA CCT GGA AAT GAA ACT AAC TGT GTA        1634
Leu Thr Phe Trp Ala Ser Gly Glu Pro Gly Asn Glu Thr Asn Cys Val
525                 530                 535

TAT ATG GAC ATC CAA GAT CAG TTG CAG TCT GTG TGG AAA ACC AAG TCA        1682
Tyr Met Asp Ile Gln Asp Gln Leu Gln Ser Val Trp Lys Thr Lys Ser
540                 545                 550                 555

TGT TTT CAG CCC TCA AGT TTT GCT TGC ATG ATG GAT CTG TCA GAC AGA        1730
Cys Phe Gln Pro Ser Ser Phe Ala Cys Met Met Asp Leu Ser Asp Arg
                560                 565                 570

AAT AAA GCC AAA TGC GAT GAT CCT GGA TCA CTG GAA AAT GGA CAC GCC        1778
Asn Lys Ala Lys Cys Asp Asp Pro Gly Ser Leu Glu Asn Gly His Ala
            575                 580                 585

ACA CTT CAT GGA CAA AGT ATT GAT GGG TTC TAT GCT GGT TCT TCT ATA        1826
Thr Leu His Gly Gln Ser Ile Asp Gly Phe Tyr Ala Gly Ser Ser Ile
                590                 595                 600

AGG TAC AGC TGT GAG GTT CTC CAC TAC CTC AGT GGA ACT GAA ACC GTA        1874
Arg Tyr Ser Cys Glu Val Leu His Tyr Leu Ser Gly Thr Glu Thr Val
605                 610                 615

ACT TGT ACA ACA AAT GGC ACA TGG AGT GCT CCT AAA CCT CGA TGT ATC        1922
Thr Cys Thr Thr Asn Gly Thr Trp Ser Ala Pro Lys Pro Arg Cys Ile
620                 625                 630                 635

AAA GTC ATC ACC TGC CAA AAC CCC CCT GTA CCA TCA TAT GGT TCT GTG        1970
Lys Val Ile Thr Cys Gln Asn Pro Pro Val Pro Ser Tyr Gly Ser Val
                640                 645                 650

GAA ATC AAA CCC CCA AGT CGG ACA AAC TCG ATA AGT CGT GTT GGG TCA        2018
Glu Ile Lys Pro Pro Ser Arg Thr Asn Ser Ile Ser Arg Val Gly Ser
            655                 660                 665

CCT TTC TTG AGG TTG CCA CGG TTA CCC CTC CCA TTA GCT AGA GCA GCC        2066
Pro Phe Leu Arg Leu Pro Arg Leu Pro Leu Pro Leu Ala Arg Ala Ala
                670                 675                 680

AAA CCT CCT CCA AAA CCT AGA TCC TCA CAA CCC TCT ACT GTG GAC TTG        2114
Lys Pro Pro Pro Lys Pro Arg Ser Ser Gln Pro Ser Thr Val Asp Leu
685                 690                 695

GCT TCT AAA GTT AAA CTA CCT GAA GGT CAT TAC CGG GTA GGG TCT CGA        2162
Ala Ser Lys Val Lys Leu Pro Glu Gly His Tyr Arg Val Gly Ser Arg
700                 705                 710                 715

GCC ATC TAC ACG TGC GAG TCG AGA TAC TAC GAA CTA CTT GGA TCT CAA        2210
Ala Ile Tyr Thr Cys Glu Ser Arg Tyr Tyr Glu Leu Leu Gly Ser Gln
                720                 725                 730

GGC AGA AGA TGT GAC TCT AAT GGA AAC TGG AGT GGT CGG CCA GCG AGC        2258
Gly Arg Arg Cys Asp Ser Asn Gly Asn Trp Ser Gly Arg Pro Ala Ser
            735                 740                 745

TGT ATT CCA GTT TGT GGA CGG TCA GAC TCT CCT CGT TCT CCT TTT ATC        2306
Cys Ile Pro Val Cys Gly Arg Ser Asp Ser Pro Arg Ser Pro Phe Ile
                750                 755                 760

TGG AAT GGG AAT TCT ACA GAA ATA GGT CAG TGG CCG TGG CAG GCA GGA        2354
Trp Asn Gly Asn Ser Thr Glu Ile Gly Gln Trp Pro Trp Gln Ala Gly
765                 770                 775

ATC TCT AGA TGG CTT GCA GAC CAC AAT ATG TGG TTT CTC CAG TGT GGA        2402
Ile Ser Arg Trp Leu Ala Asp His Asn Met Trp Phe Leu Gln Cys Gly
780                 785                 790                 795

GGA TCT CTA TTG AAT GAG AAA TGG ATC GTC ACT GCT GCC CAC TGT GTC        2450
Gly Ser Leu Leu Asn Glu Lys Trp Ile Val Thr Ala Ala His Cys Val
                800                 805                 810

ACC TAC TCT GCT ACT GCT GAG ATT ATT GAC CCC AAT CAG TTT AAA ATG        2498
Thr Tyr Ser Ala Thr Ala Glu Ile Ile Asp Pro Asn Gln Phe Lys Met
                815                 820                 825

TAT CTG GGC AAG TAC TAC CGT GAT GAC AGT AGA GAC GAT GAC TAT GTA        2546
Tyr Leu Gly Lys Tyr Tyr Arg Asp Asp Ser Arg Asp Asp Asp Tyr Val
            830                 835                 840
```

| | | |
|---|---|---|
| CAA GTA AGA GAG GCT CTT GAG ATC CAC GTG AAT CCT AAC TAC GAC CCC<br>Gln Val Arg Glu Ala Leu Glu Ile His Val Asn Pro Asn Tyr Asp Pro<br>       845                   850                855 | 2594 |
| GGC AAT CTC AAC TTT GAC ATA GCC CTA ATT CAA CTG AAA ACT CCT GTT<br>Gly Asn Leu Asn Phe Asp Ile Ala Leu Ile Gln Leu Lys Thr Pro Val<br>860                   865                 870                875 | 2642 |
| ACT TTG ACA ACA CGA GTC CAA CCA ATC TGT CTG CCT ACT GAC ATC ACA<br>Thr Leu Thr Thr Arg Val Gln Pro Ile Cys Leu Pro Thr Asp Ile Thr<br>                 880                   885                890 | 2690 |
| ACA AGA GAA CAC TTG AAG GAG GGA ACA TTA GCA GTG GTG ACA GGT TGG<br>Thr Arg Glu His Leu Lys Glu Gly Thr Leu Ala Val Val Thr Gly Trp<br>               895                   900                905 | 2738 |
| GGT TTG AAT GAA AAC AAC ACC TAT TCA GAG ACG ATT CAA CAA GCT GTG<br>Gly Leu Asn Glu Asn Asn Thr Tyr Ser Glu Thr Ile Gln Gln Ala Val<br>910                   915                 920 | 2786 |
| CTA CCT GTT GTT GCA GCC AGC ACC TGT GAA GAG GGG TAC AAG GAA GCA<br>Leu Pro Val Val Ala Ala Ser Thr Cys Glu Glu Gly Tyr Lys Glu Ala<br>               925                   930                935 | 2834 |
| GAC TTA CCA CTG ACA GTA ACA GAG AAC ATG TTC TGT GCA GGT TAC AAG<br>Asp Leu Pro Leu Thr Val Thr Glu Asn Met Phe Cys Ala Gly Tyr Lys<br>940                   945                 950           955 | 2882 |
| AAG GGA CGT TAT GAT GCC TGC AGT GGG GAC AGT GGA GGA CCT TTA GTG<br>Lys Gly Arg Tyr Asp Ala Cys Ser Gly Asp Ser Gly Gly Pro Leu Val<br>               960                   965                970 | 2930 |
| TTT GCT GAT GAT TCC CGT ACC GAA AGG CGG TGG GTC TTG GAA GGG ATT<br>Phe Ala Asp Asp Ser Arg Thr Glu Arg Arg Trp Val Leu Glu Gly Ile<br>               975                   980                985 | 2978 |
| GTC AGC TGG GGC AGT CCC AGT GGA TGT GGC AAG GCG AAC CAG TAC GGG<br>Val Ser Trp Gly Ser Pro Ser Gly Cys Gly Lys Ala Asn Gln Tyr Gly<br>               990                   995             1000 | 3026 |
| GGC TTC ACT AAA GTT AAC GTT TTC CTG TCA TGG ATT AGG CAG TTC ATT<br>Gly Phe Thr Lys Val Asn Val Phe Leu Ser Trp Ile Arg Gln Phe Ile<br>1005                1010                1015 | 3074 |
| TGAAACTGAT CTAAATATTT TAAGCATGGT TATAAACGTC TTGTTTCCTA TTATTGCTTT | 3134 |
| ACTAGTTTAA CCCATAAGAA GGTTAACTGG GTAAGGCACA AGGATCATTG TTTCTGTTTG | 3194 |
| TTTTTACAAA TGGTTATTTT AGTCAGTGAA TGAGAATAGT ATCCATTGAA GACTGTTACC | 3254 |
| TTTTATTCTA CCTTTTTATA TTACTATGTA AGTATTTGGG ATATCTTCTA CACATGAAAA | 3314 |
| TTCTGTCATT TTACCATAAA TTTGGTTTCT GGTGTGTGCT AAGTCCACCA GTAGAGAACG | 3374 |
| ATGTAATTTT CACTAGCACA TGAAATAAAT ATAGAACAAA TCTATTATAA ACTACCTTAA | 3434 |
| AAAAAAAAAA AAAA | 3448 |

(2) INFORMATION FOR SEQ ID NO:4:

(i) SEQUENCE CHARACTERISTICS:
        (A) LENGTH: 1019 amino acids
        (B) TYPE: amino acid
        (D) TOPOLOGY: linear (ii) MOLECULE TYPE: protein (xi) SEQUENCE DESCRIPTION: SEQ ID NO:4:

Met Val Leu Ala Ser Phe Leu Val Ser Gly Leu Val Leu Gly Leu Leu
 1              5                  10                15

Ala Gln Lys Met Arg Pro Val Gln Ser Lys Gly Val Asp Leu Gly Leu
            20                  25                  30

Cys Asp Glu Thr Arg Phe Glu Cys Lys Cys Gly Asp Pro Gly Tyr Val
        35                    40                  45

```
Phe Asn Ile Pro Val Lys Gln Cys Thr Tyr Phe Tyr Arg Trp Arg Pro
 50                  55                  60
Tyr Cys Lys Pro Cys Asp Asp Leu Glu Ala Lys Asp Ile Cys Pro Lys
 65                  70                  75                  80
Tyr Lys Arg Cys Gln Glu Cys Lys Ala Gly Leu Asp Ser Cys Val Thr
                 85                  90                  95
Cys Pro Pro Asn Lys Tyr Gly Thr Trp Cys Ser Gly Glu Cys Gln Cys
                100                 105                 110
Lys Asn Gly Gly Ile Cys Asp Gln Arg Thr Gly Ala Cys Ala Cys Arg
                115                 120                 125
Asp Arg Tyr Glu Gly Val His Cys Glu Ile Leu Lys Gly Cys Pro Leu
130                 135                 140
Leu Pro Ser Asp Ser Gln Val Gln Glu Val Arg Asn Pro Pro Asp Asn
145                 150                 155                 160
Pro Gln Thr Ile Asp Tyr Ser Cys Ser Pro Gly Phe Lys Leu Lys Gly
                165                 170                 175
Met Ala Arg Ile Ser Cys Leu Pro Asn Gly Gln Trp Ser Asn Phe Pro
                180                 185                 190
Pro Lys Cys Ile Arg Glu Cys Ala Met Val Ser Ser Pro Glu His Gly
                195                 200                 205
Lys Val Asn Ala Leu Ser Gly Asp Met Ile Glu Gly Ala Thr Leu Arg
210                 215                 220
Phe Ser Cys Asp Ser Pro Tyr Tyr Leu Ile Gly Gln Glu Thr Leu Thr
225                 230                 235                 240
Cys Gln Gly Asn Gly Gln Trp Asn Gly Gln Ile Pro Gln Cys Lys Asn
                245                 250                 255
Leu Val Phe Cys Pro Asp Leu Asp Pro Val Asn His Ala Glu His Lys
                260                 265                 270
Val Lys Ile Gly Val Glu Gln Lys Tyr Gly Gln Phe Pro Gln Gly Thr
                275                 280                 285
Glu Val Thr Tyr Thr Cys Ser Gly Asn Tyr Phe Leu Met Gly Phe Asp
290                 295                 300
Thr Leu Lys Cys Asn Pro Asp Gly Ser Trp Ser Gly Ser Gln Pro Ser
305                 310                 315                 320
Cys Val Lys Val Ala Asp Arg Glu Val Asp Cys Asp Ser Lys Ala Val
                325                 330                 335
Asp Phe Leu Asp Asp Val Gly Glu Pro Val Arg Ile His Cys Pro Ala
                340                 345                 350
Gly Cys Ser Leu Thr Ala Gly Thr Val Trp Gly Thr Ala Ile Tyr His
                355                 360                 365
Glu Leu Ser Ser Val Cys Arg Ala Ala Ile His Ala Gly Lys Leu Pro
370                 375                 380
Asn Ser Gly Gly Ala Val His Val Val Asn Asn Gly Pro Tyr Ser Asp
385                 390                 395                 400
Phe Leu Gly Ser Asp Leu Asn Gly Ile Lys Ser Glu Glu Leu Lys Ser
                405                 410                 415
Leu Ala Arg Ser Phe Arg Phe Asp Tyr Val Arg Ser Ser Thr Ala Gly
                420                 425                 430
Lys Ser Gly Cys Pro Asp Gly Trp Phe Glu Val Asp Glu Asn Cys Val
                435                 440                 445
Tyr Val Thr Ser Lys Gln Arg Ala Trp Glu Arg Ala Gln Gly Val Cys
                450                 455                 460
Thr Asn Met Ala Ala Arg Leu Ala Val Leu Asp Lys Asp Val Ile Pro
465                 470                 475                 480
```

-continued

```
Asn Ser Leu Thr Glu Thr Leu Arg Gly Lys Gly Leu Thr Thr Thr Trp
            485                 490                 495

Ile Gly Leu His Arg Leu Asp Ala Glu Lys Pro Phe Ile Trp Glu Leu
            500                 505                 510

Met Asp Arg Ser Asn Val Val Leu Asn Asp Asn Leu Thr Phe Trp Ala
            515                 520                 525

Ser Gly Glu Pro Gly Asn Glu Thr Asn Cys Val Tyr Met Asp Ile Gln
530                 535                 540

Asp Gln Leu Gln Ser Val Trp Lys Thr Lys Ser Cys Phe Gln Pro Ser
545                 550                 555                 560

Ser Phe Ala Cys Met Met Asp Leu Ser Asp Arg Asn Lys Ala Lys Cys
            565                 570                 575

Asp Asp Pro Gly Ser Leu Glu Asn Gly His Ala Thr Leu His Gly Gln
            580                 585                 590

Ser Ile Asp Gly Phe Tyr Ala Gly Ser Ser Ile Arg Tyr Ser Cys Glu
            595                 600                 605

Val Leu His Tyr Leu Ser Gly Thr Glu Thr Val Thr Cys Thr Thr Asn
            610                 615                 620

Gly Thr Trp Ser Ala Pro Lys Pro Arg Cys Ile Lys Val Ile Thr Cys
625                 630                 635                 640

Gln Asn Pro Pro Val Pro Ser Tyr Gly Ser Val Glu Ile Lys Pro Pro
            645                 650                 655

Ser Arg Thr Asn Ser Ile Ser Arg Val Gly Ser Pro Phe Leu Arg Leu
            660                 665                 670

Pro Arg Leu Pro Leu Pro Leu Ala Arg Ala Ala Lys Pro Pro Pro Lys
            675                 680                 685

Pro Arg Ser Ser Gln Pro Ser Thr Val Asp Leu Ala Ser Lys Val Lys
690                 695                 700

Leu Pro Glu Gly His Tyr Arg Val Gly Ser Arg Ala Ile Tyr Thr Cys
705                 710                 715                 720

Glu Ser Arg Tyr Tyr Glu Leu Leu Gly Ser Gln Gly Arg Arg Cys Asp
            725                 730                 735

Ser Asn Gly Asn Trp Ser Gly Arg Pro Ala Ser Cys Ile Pro Val Cys
            740                 745                 750

Gly Arg Ser Asp Ser Pro Arg Ser Pro Phe Ile Trp Asn Gly Asn Ser
            755                 760                 765

Thr Glu Ile Gly Gln Trp Pro Trp Gln Ala Gly Ile Ser Arg Trp Leu
            770                 775                 780

Ala Asp His Asn Met Trp Phe Leu Gln Cys Gly Gly Ser Leu Leu Asn
785                 790                 795                 800

Glu Lys Trp Ile Val Thr Ala Ala His Cys Val Thr Tyr Ser Ala Thr
            805                 810                 815

Ala Glu Ile Ile Asp Pro Asn Gln Phe Lys Met Tyr Leu Gly Lys Tyr
            820                 825                 830

Tyr Arg Asp Asp Ser Arg Asp Asp Tyr Val Gln Val Arg Glu Ala
            835                 840                 845

Leu Glu Ile His Val Asn Pro Asn Tyr Asp Pro Gly Asn Leu Asn Phe
850                 855                 860

Asp Ile Ala Leu Ile Gln Leu Lys Thr Pro Val Thr Leu Thr Thr Arg
865                 870                 875                 880

Val Gln Pro Ile Cys Leu Pro Thr Asp Ile Thr Thr Arg Glu His Leu
            885                 890                 895

Lys Glu Gly Thr Leu Ala Val Val Thr Gly Trp Gly Leu Asn Glu Asn
```

-continued

```
                    900                 905                 910
Asn Thr Tyr Ser Glu Thr Ile Gln Gln Ala Val Leu Pro Val Val Ala
        915                 920                 925

Ala Ser Thr Cys Glu Glu Gly Tyr Lys Glu Ala Asp Leu Pro Leu Thr
        930                 935                 940

Val Thr Glu Asn Met Phe Cys Ala Gly Tyr Lys Lys Gly Arg Tyr Asp
945                 950                 955                 960

Ala Cys Ser Gly Asp Ser Gly Gly Pro Leu Val Phe Ala Asp Asp Ser
                965                 970                 975

Arg Thr Glu Arg Arg Trp Val Leu Glu Gly Ile Val Ser Trp Gly Ser
                980                 985                 990

Pro Ser Gly Cys Gly Lys Ala Asn Gln Tyr Gly Gly Phe Thr Lys Val
        995                 1000                1005

Asn Val Phe Leu Ser Trp Ile Arg Gln Phe Ile
        1010                1015
```

EXPRESSION OF *CARCINOSCORPIUS ROTUNDICAUDA* FACTOR C IN EUKARYOTES

This application is a divisional of application Ser. No. 08/596,405 now U.S. Pat. No. 5,858,706, filed on Feb. 2, 1996, which is a continuation in part of application Ser. No. 08/296,014 filed Aug. 19, 1994, now U.S. Pat. No. 5,716,834 the entire contents of which are hereby incorporated by reference.

RELATED APPLICATIONS

The present application is a Continuation-In-Part of co-pending application U.S. Ser. No. 08/296,014, filed Aug. 19, 1994, the entire contents of which are hereby incorporated by reference.

FIELD OF THE INVENTION

The present application relates to recombinant Factor C of the horseshoe crab *Carcinoscorpius rotundicauda* (CrFC), especially with respect to its expression in eukaryotes. The present application also relates to the use of the CrFC as an affinity reagent for binding of endotoxin. Endotoxin bound by CrFC can be removed from materials in instances where it is desirable to prepare a material free of endotoxin.

BACKGROUND OF THE INVENTION

Articles of the scientific periodical and patent literature are cited throughout the specification. Each such article is hereby incorporated by reference in its entirety by such citation.

Gram negative bacterial endotoxin is a widespread contaminant of materials employed in biomedical arts, both research and clinical. All pharmaceutical solutions used for parenteral or injection administration must be certified as to endotoxin levels. Also, media used for tissue culture applications are typically tested for the presence of endotoxin. It is of great importance, therefore, to be able to produce a reliably reproducible test for the presence of endotoxin in a sample. Also, it would be an advance in the art to provide materials and methods for removing Gram negative bacterial endotoxins from formulations intended for pharmaceutical or other uses requiring preparations substantially free of endotoxin.

Factor C is a component of the Limulus amoebocyte lysate (LAL) assay that is presently the standard method for testing for endotoxin. Factor C is a serine protease proenzyme that is the first protein in a cascade that leads to coagulation of the LAL upon contact with endotoxin. Factor C is the protein that actually binds to the endotoxin; upon binding of endotoxin, the serine protease activity of Factor C becomes activated. The activated Factor C initiates a chain of proteolytic steps culminating in formation of a solid clot of protein from the LAL. The time for forming the LAL clot and the degree of gelation is indicative of the amount of endotoxin in a sample (Ho, B., Kim, J. C., and Ding, J. L., 1993, Biochem. Mol. Biol. Intl. 29, 687–694). However, this gelation assay is subjective, and variable in its sensitivity of detection of endotoxin due to batch-to-batch variation in the amoebocyte lysate preparation. It is therefore desirable to express recombinant Factor C which could be standardized for use in an assay for endotoxin detection.

There are other endotoxin tests presently known, for example, the United States Pharmacopeia (USP) rabbit pyrogen assay (Tomasulo, P A., Levin, J. Murphy, P A. & Winkelstein, J A. 1977. J. Lab. Clin. Met. 89, 308–315). However, the USP rabbit pyrogen test is not only time consuming, it is also expensive and often gives variable results in detecting endotoxin in pharmaceuticals and parentals (Muller-Calgon, H., pp. 343–356; "Endotoxins and their Detection with the LAL test," S. Watson et al., ed., c. 1982 by Alan R. Liss, New York N.Y.).

Enzyme-linked-immunosorbent assay (ELISA) has been developed for testing evoked secretion of interleukin-6 from monocytic cell lines in response to pyrogen or endotoxin (Taktak, Y. S., Selkirk, S., Bristow, A F., Carpenter, A., Ball, C., Rafferty, B., & Poole, S.,*J. Pharm. Pharmacol.* 43, 578–582 (1991)). However, this test is probably more suited for research purposes.

One other form of endotoxin detection involves its localization in tissues of experimental animals during induced endotoxemia. An immunohistochemical method utilizes native Factor C (purified from *T. tridentatus*) to specifically bind the endotoxin. The Factor C-endotoxin complex is then revealed by labelled anti-Factor C antibody (Takeuchi, M. et al., *Pathol. Res. Pract.* 190(12): 1123–1133 (1994); Nakao, A. et al., *Eur. Surg. Res.* 27(4): 216–221 (1995)). This study indicates another utility for Factor C. It is therefore within the embodiment of this application to obtain truncated recombinant constructs (e.g., pHILD2/CrFC21/EE containing the 5' end of CrFC cDNA insert flanked by EcoR1 sites).

cDNAs encoding Factor C proteins from *Carcinoscorpius rotundicauda* have been previously described (U.S. Ser. No. 08/296,014 and J. L. Ding, A. A. Navas III and B. Ho, *Mol. Marine Biol. and Biotech.* 4:90–103 (1995)). Recombinant Factor C from Carcinoscorpius rotundicauda (rCrFC) has been produced in vitro by coupled transcription/translation systems (U.S. Ser. No. 08/296,014 and S. D. Roopashree et al. *Biochem. and Mol. Biol. Int'l.* 35:841–849 (1995)). However, the present invention resides partly in the development of in vivo systems, especially using yeasts as a host cell, for efficient production of rCrFC by expression of cloned DNA.

Also, the protection of rCrFC from activation and subsequent self-proteolysis by binding of endotoxin which may be present in solutions used in isolation of the protein is described in U.S. Ser. No. 08/296,014. Basically, dimethylsulfoxide ($Me_2SO$, DMSO) is added to solutions which are used during the purification process. Even greater protection of the rCrFC is achieved by also adding an agent effective for chelating divalent metal ions to the purification solutions.

As a means to circumvent difficulties in determining endotoxin in plasma due to endogenous interfering factors, a chromogenic LAL assay was modified to include a specific step to adsorb the plasma endotoxin using immobilized histidine. Endotoxin in samples was separated from interfering factors by chromatography through immobilized histidine in which endotoxin was specifically adsorbed and, subsequently quantified by fluorimetric LAL assay (Nawata, M., Minobe, S., Hase, M., Watanabe, T., Sato, T. & Tosa, T., *J. Chromatogr.*, 597: 415–424 (1992); Minobe, S., Nawata, M., Shigemori, N. & Watanabe, T.,*Eur. J. Clin. Chem. Clin. Biochem.*, 32(10): 797–803 (1994). However, this method of endotoxin adsorption is limited only to small volumes of 0.5–1 ml, and there is no report on the use or feasibility of this method for removing endotoxin from large preparations. It has so far only been reported as an improved method of endotoxin assay, albeit one limited by infeasibility of chromogenic assay of the endotoxin bound to the column.

More recently, Qiagen (US) has marketed a 'Qiagen' kit for purification of endotoxin-free plasmids (See, *Qiagen News Issue* No. 1, 1996). This may involve a specific (proprietary) reagent that removes endotoxin from the plasmid preparation.

SUMMARY OF THE INVENTION

Purified CrFC is found to be a useful protein, both as a component of a test for endotoxins and as an affinity reagent for removal of endotoxins from other materials. Thus, one object of the present invention is to provide purified recombinant CrFC. The present invention is also embodied in vectors for expressing recombinant CrFC in eukaryotic host cells, such as mammalian cells and yeasts. The present invention is further embodied by eukaryotic host cells expressing recombinant CrFC and methods for purifying recombinant CrFC which utilize cells transformed with DNA cloned in a eukaryotic expression vector to synthesize the recombinant CrFC protein (rCrFC). In particular, it is an object of the present invention to express CrFC in host cells that do not produce bacterial endotoxin and are capable of expressing large quantities of CrFC.

cDNAs appropriate for expression in the presently-described system can be cDNAs encoding Factor C of any horseshoe crab. Two representative nucleotide sequences are presented as SEQ. I.D. NO. 1 and SEQ. I.D. NO. 3. A cDNA encoding the Factor C of Tachypleus tridentatus is disclosed by Muta et al. (*The Journal of Biol. Chem.* 266(10):6554–6561 (1991)).

In many instances, it is desirable to prepare materials, such as culture media or injection formulations or the like, that are substantially free of endotoxin contamination. Thus, it is a further object of the invention to provide affinity reagents for removing endotoxin from materials. It is another object of the present invention to provide methods for removing endotoxin from materials, wherein such methods employ an affinity reagent comprising CrFC.

The present methods for testing for endotoxin in a sample have many drawbacks, but two principal drawbacks are lot-to-lot variation of LAL preparations and the somewhat subjective nature of the test. Thus, the present invention, by providing tests for endotoxin that rely only upon the use of Factor C, rather than upon clotting of a LAL, eliminate these drawbacks. In particular, it is an object of the present invention to provide affinity assay methods for detection and quantitation of endotoxin in a sample. Because the assays utilize rCrFC of consistent composition, they are less subject to lot-to-lot variation. Because the assays are performed in a format that is quantitative, the assays are more objective than assays that rely upon a determination that a clot has formed in a LAL.

BRIEF DESCRIPTION OF THE DRAWINGS

FIG. 4 shows the construct pHILD2/CrFC21. The EcoRI flanking fragment of CrFC21 from pGEM11Zf(+)/CrFC21 was ligated to the EcoRI linearized *P. pastoris* expression vector, pHILD2 (InVitrogen Corp., San Diego, Calif.), to generate the intermediate construct pHILD2/EE21. This construct was linearized with XhoI to accommodate the XhoI flanking portion of the cDNA from the plasmid pCDNA1/CrFC21 (see FIG. 1) to result in pHILD2/CrFC21. This construct contains 3448 bp of CrFC21 cDNA.

FIG. 5A shows Northern hybridization of Factor C transcripts from clone #8 containing pHILD2/CrFC21. The EcoRI flanking fragment of CrFC21 was $^{32}$P-labelled to high specific activity and used as a probe. The level of transcription was monitored over close time intervals of induction with methanol which was added at time zero (at the start) and at 24 h. CrFC MRNA appeared as early as 1 hour with peak accumulation at 5 hours after induction. No further increase in CrFC mRNA was seen after the second methanol induction.

Lanes: 1, 4, 7 & 10 show 48 hours of induction;

2, 5, 8 & 11 show 26 hours of induction;

3, 6, 9 & 12 show 8 hours of induction;

13 shows expression of negative control DNA.

Figure 6:
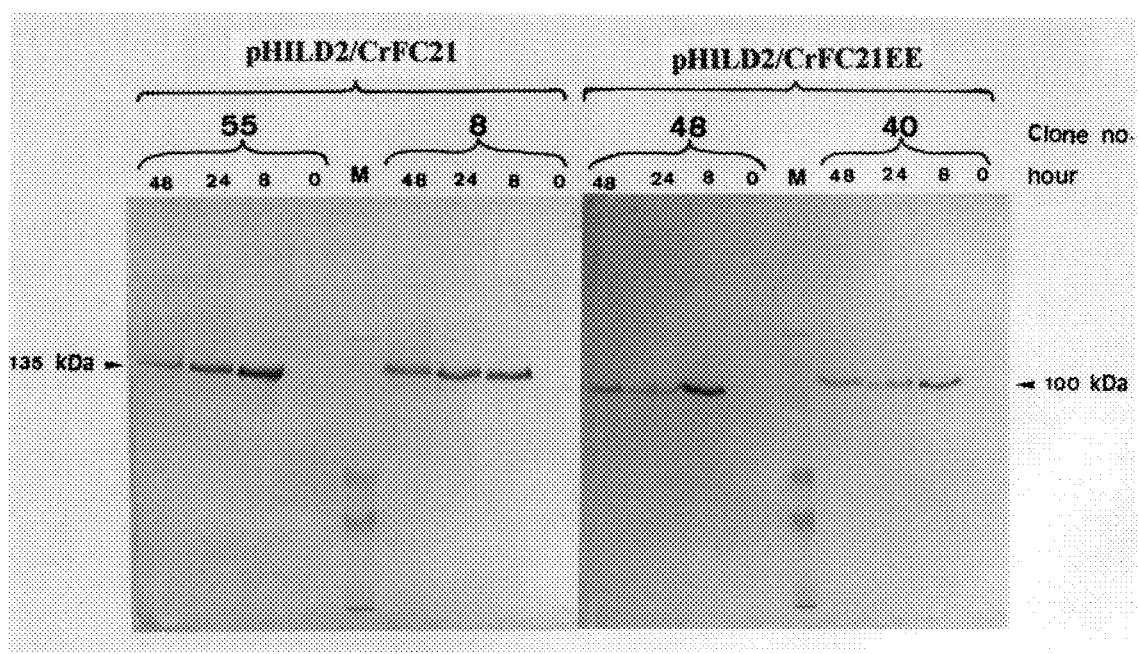

FIG. 6 shows Western blot analysis of rCrFC from methanol-induced *P. pastoris* containing pHILD2/CrFC21. Clones No. 8 and No. 55 (harboring CrFC21 full-length cDNA) and clones No. 40 and No. 48 (harboring CrFC21EE, a truncated CrFC21 fragment flanked by EcoRI sites) were induced for up to 48 hours on minimal media, and subjected to glass bead treatment followed by electrophoresis of 100 μg of each sample on reducing SDS/β-mercaptoethanol polyacrylamide gel. The electroblotted proteins were probed with anti-Factor C antibodies. Clone #8 yielded the highest level of rCrFC which was found to have a molecular weight of ~135 kDa. Based on the 991 amino acid sequence of the insert, the expected size of the protein would have been about 109 kDa. The difference in the size of the Factor C could be attributable to glycosylation of the recombinant product in the yeast host. Clones No. 40 and No. 48 produced smaller truncated rCrFC proteins of 100 kDa. The results show that the maximal level of rCrFC expression occurred within 8 hours after the start of methanol induction.

Figure 7:
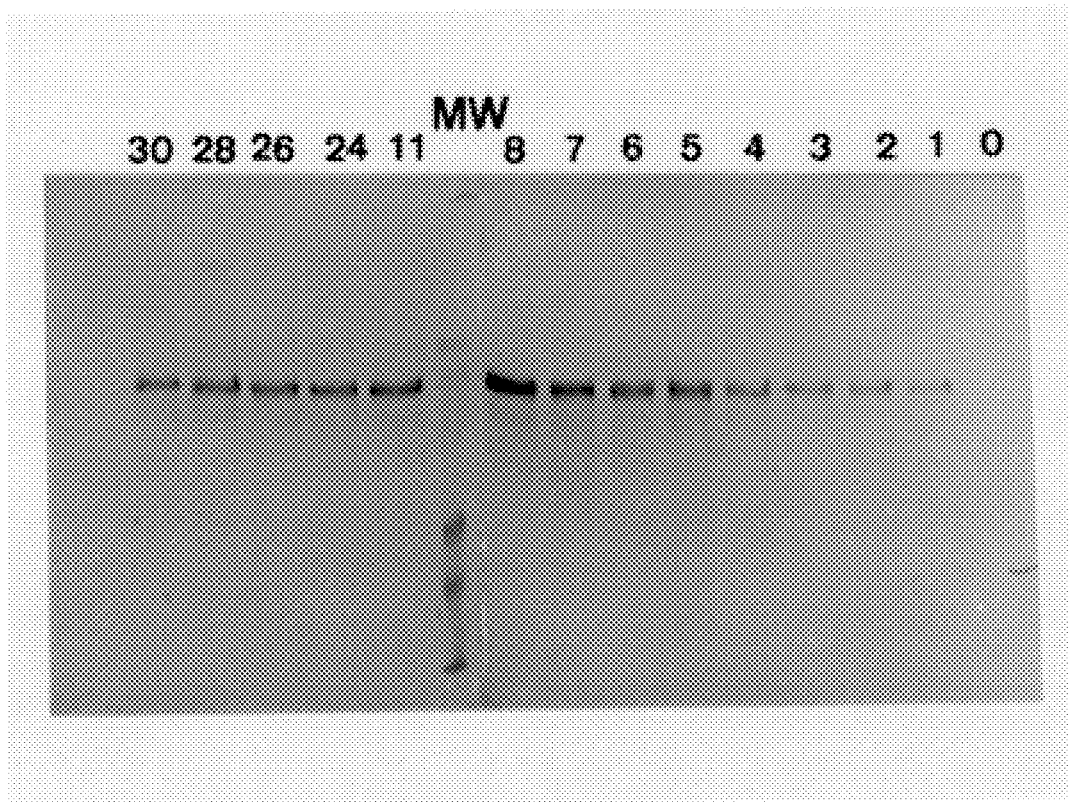

FIG. 7 shows rCrFC produced from *P. pastoris* clone #8 over a time course of methanol-induction at 30° C. The culture was induced twice with 0.5% methanol at time zero and 24 hours. Cell samples were collected at the time period indicated. After glass bead treatment, the cell homogenate was centrifuged at 12,000×g for 30 min. The supernatant was kept separately. The pellets were resuspended in breaking buffer (1:10 v/v). Aliquots of the suspension were boiled in SDS/β-mercaptoethanol and resolved by electrophoresis on 10% acrylamide gels containing SDS. From such close time points of sampling, we confirm that the maximal synthesis of rCrFC occurred at 8 hours. The molecular weight markers (MW) were obtained from BioRad (Kaleidoscope) of sizes 208, 144, 87, 44.1, 32.7 and 17.7 kDa.

Figure 8A:
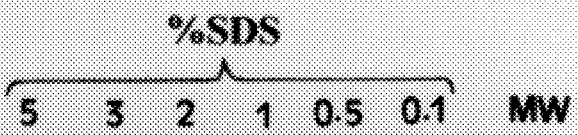
Figure 8B:

FIGS. 8A, 8B show detergent solubilization of rCrFC obtained from transformed P. pastoris (clone #8: PHILD2/CrFC21). After overnight solubilization with increasing concentrations of the detergents, the homogenate was centrifuged and 100 μg soluble protein of each supernatant was analyzed by Western blot. FIG. 8A shows that solubilization was effective from 1% SDS to higher concentrations. FIG. 8B shows that solubilization was achieved from 1% of sarkosyl to higher concentrations. MW is the molecular weight markers (BioRad Kaleidoscope), of 208, 144, 87, 44.1, 32.7, and 17.7 kDa. Lane Tp contains the total protein used for solubilization. 1M NaCl did not solubilize rCrFC.

Figure 9A:
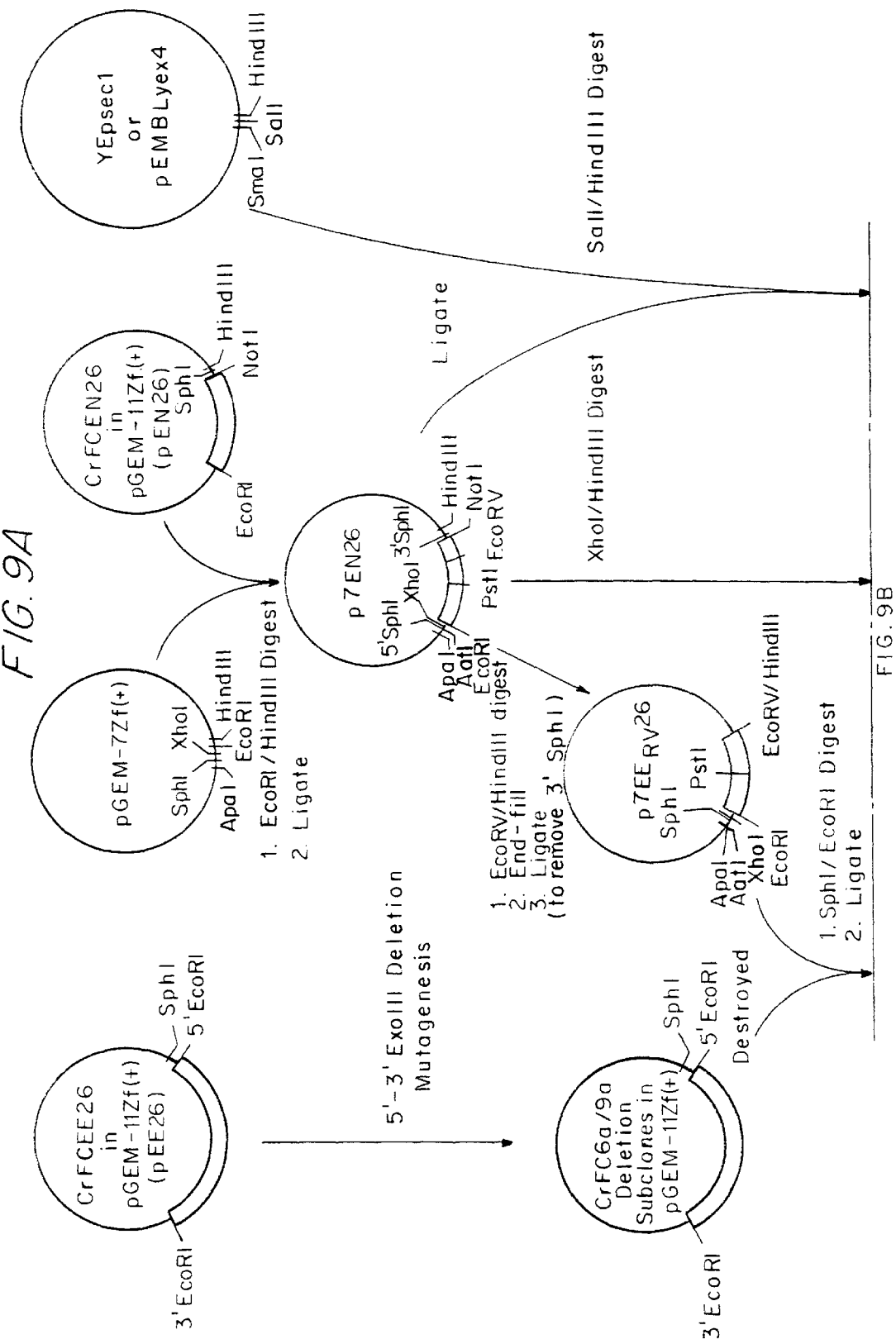
Figures 9A, 9B:
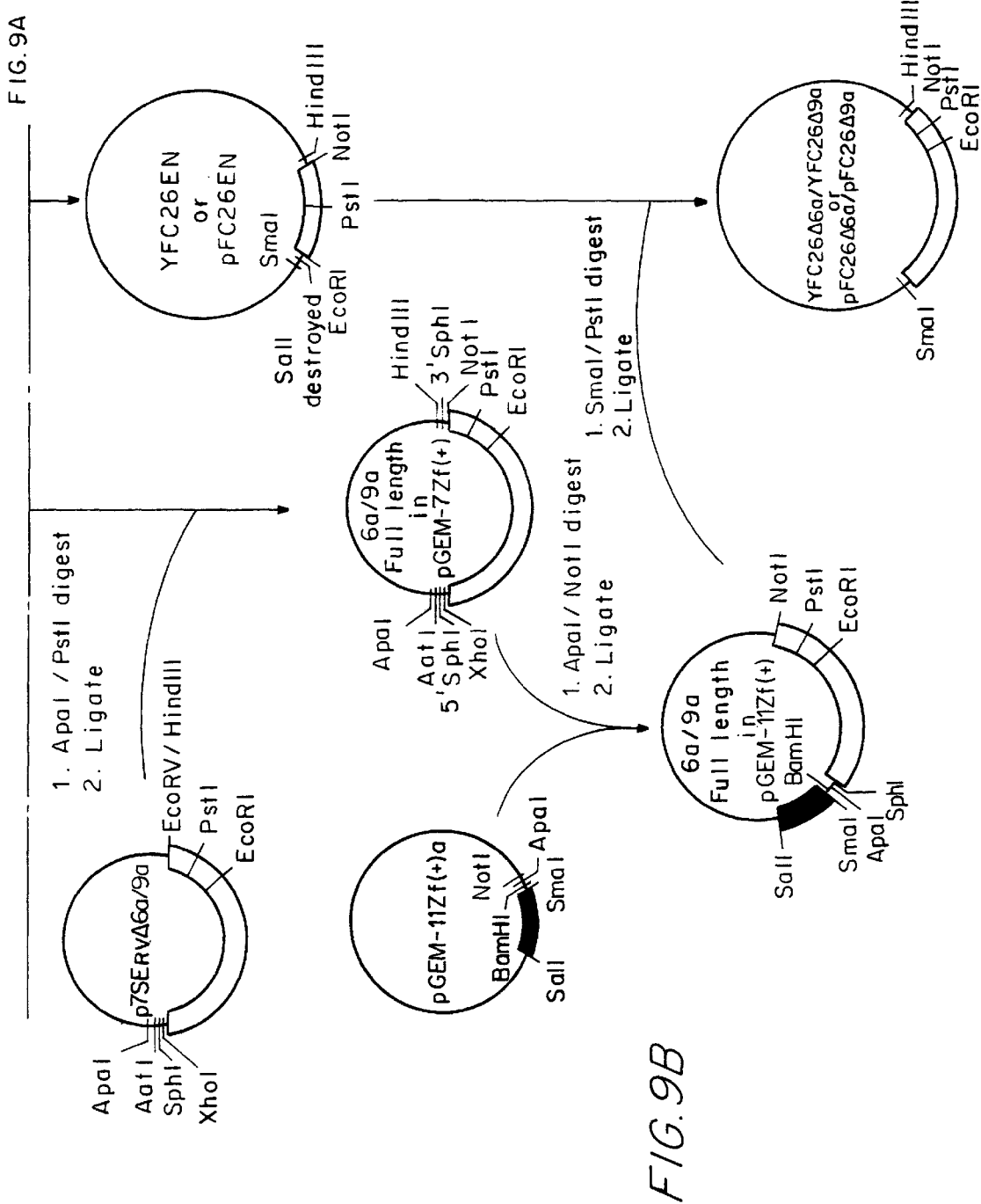

FIG. 9 shows the construction plasmids for expression of CrFC26 cDNA deletion derivatives lacking the 5' untranslated region (UTR) and portions of the leader peptide using two S. cerevisiae expression vectors, YepSec1 (secretion) and pEMBLyex4 (non-secretion). The EcoRI-EcoRI (EE) fragment and the EcoRI-NotI (EN) fragments of CrFC26 cDNA were isolated from recombinant phage clones and inserted individually into the vector PGEM11Zf(+), giving PEE26 and PEN26, respectively. The entire 5' UTR and various lengths of the sequences coding for the leader peptide of CrFC26 were deleted by performing 5'-3' Exo III deletion mutagenesis on pEE26. From the deletion library, two mutants, CrFC6a/9a, also designated FC26Δ6a, and FC26Δ9a (see FIG. 9) were selected for expression studies. The EN fragment of CrFC 26 was excised from pEN26 with EcoRI and HindIII and inserted into the vector pGEM7Zf(+) to give p7EN26. From p7EN26, the same fragment was isolated using the flanking XhoI and HindIII sites and inserted into SalI/HindIII digested YepSec1 or pEMBLyex4, giving YFC26EN or pFC26EN, respectively. The SphI-EcoRI fragments from FC26Δ6a and FC26Δ9a, viz., CrFC61/91 deletion subclones in pGEM11Zf(+) were isolated and inserted through an intermediate step, into the SphI and EcoRI sites of p7EE$_{RV}$26. The insert is thus flanked by EcoRI (E) and EcoRV (E$_{RV}$) sites. The resultant full-length deletion mutants in p7SE$_{RV}$Δ6a/9a were subcloned into pGEM11Zf(+)a, a derivative of pGEMIIZf(+) (see FIG. 10B) The SmaI-PstI fragments were subsequently isolated from these subclones and inserted into SmaI/PstI digested pFC26EN to give the plasmids pFC26Δ6a and pFC26Δ9a. The same fragments were inserted into YFC26EN, creating in-frame protein fusions to the K. lactis killer toxin signal sequence, to yield YFC26Δ61 an YPC26Δ9a.

Figure 10:
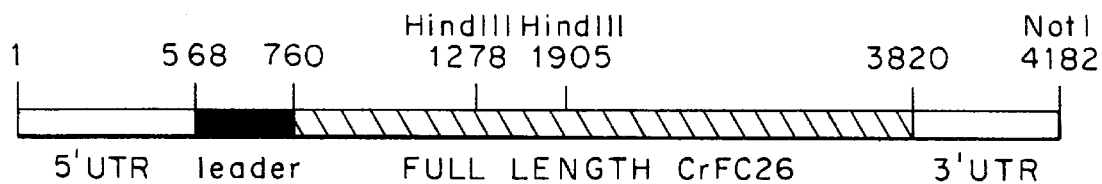
Figure 10:
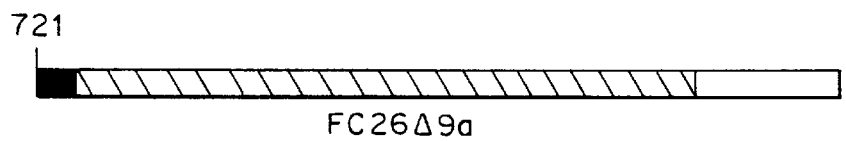
Figure 10:
Figure 10:
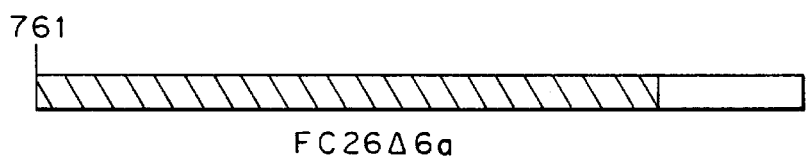
Figure 10:
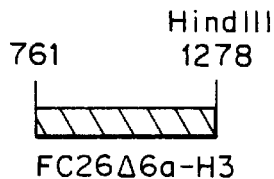
Figure 10:
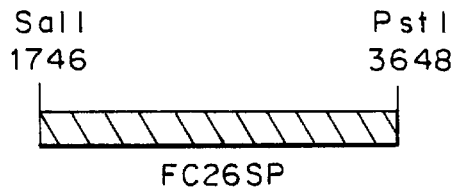

FIG. 10 shows a schematic diagram illustrating the different gene fragments from CrFC26 cDNA cloned into the S. cerevisiae expression vector, YepSec1 (Baldari, C., et al. Embo J. 6:229–234 (1987)). The complete CrFC26 cDNA (top) has been included for reference. Key: open box, untranslated region; shaded box, sequence coding for the leader peptide; hatched box, coding region. ExoIII nuclease deletion mutagenesis was carried out on CrFC26 cDNA to yield the deletion mutants FC26Δ9a and FC26Δ6a which contain 5' deletions up to nucleotide positions 721 and 761, respectively. Further deletions were carried out on FC26Δ9a and 6a by removing all of the nucleotides downstream of an internal HindIII site at nucleotide position 1278 to give FC26Δ9a-H3 and FC26Δ6a-H3, respectively. A 1902 bp internal SalI/PstI fragment of CrFC26 cDNA was inserted directly into YepSec1 in-frame with the Kluyveromyces lactis killer toxin signal sequence.

Figure 11B:
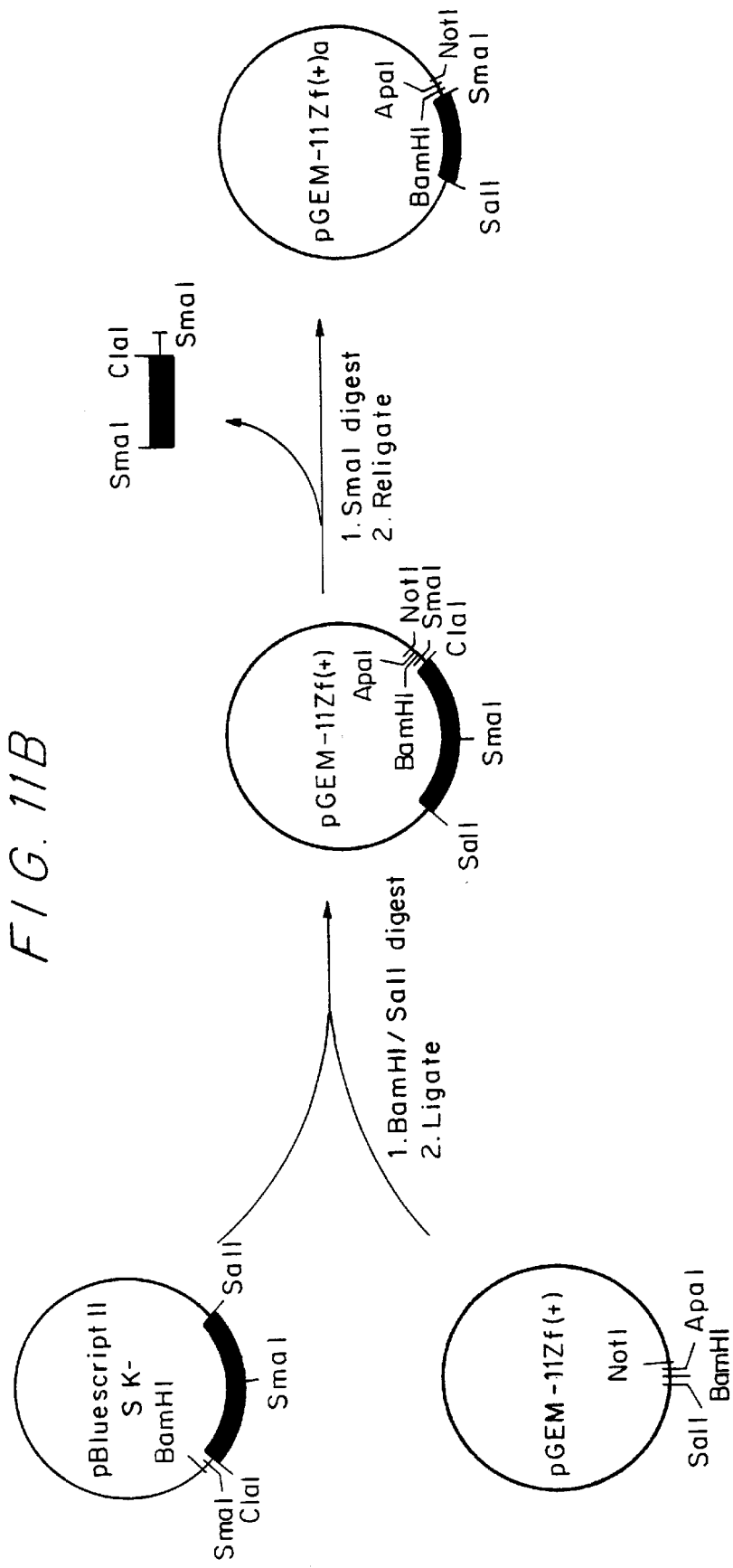

FIGS. 11A, 11B. FIG. 11A shows sequences at the junction between K. lactis killer toxin signal peptide (in YepSec1) and CrFC26 deletion mutants 6a and 9a. The K. lactis killer toxin signal peptide is linked in-frame to CrFC26 deletion mutants 6a and 9a by a short stretch of polylinker sequence derived from pGEM7Zf(+) and pGEM11Zf(+). This polylinker sequence contains an ATG codon (boxed) which would serve as a translation initiation codon in YFC26Δ6a and 9a. FIG. 11B shows construction of pGEM11Zf(+)a, a derivative of pGEM11Zf(+). A ClaI/SalI stuffer DNA fragment (shaded) was inserted into pBluescript II SK-. This fragment was then isolated by BamHI/SalI digestion and inserted into pGEM11Zf(+), effectively introducing a SmaI site into the multiple cloning site of pGEM11Zf(+). The resultant plasmid was digested with SmaI and religated, removing a 300 bp SmaI fragment to give pGEM11Zf(+)a.

Figure 12A:
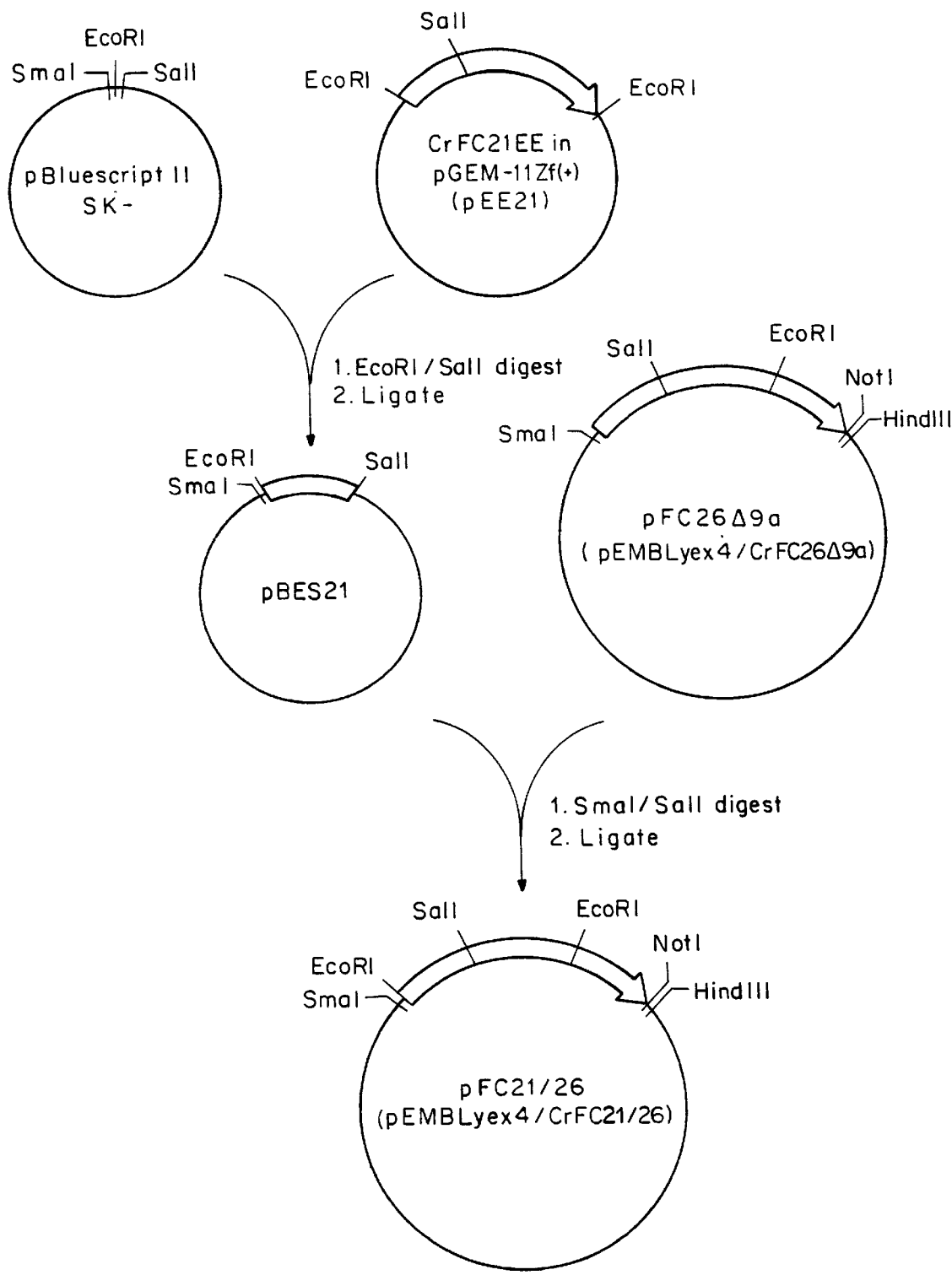
Figure 12B:
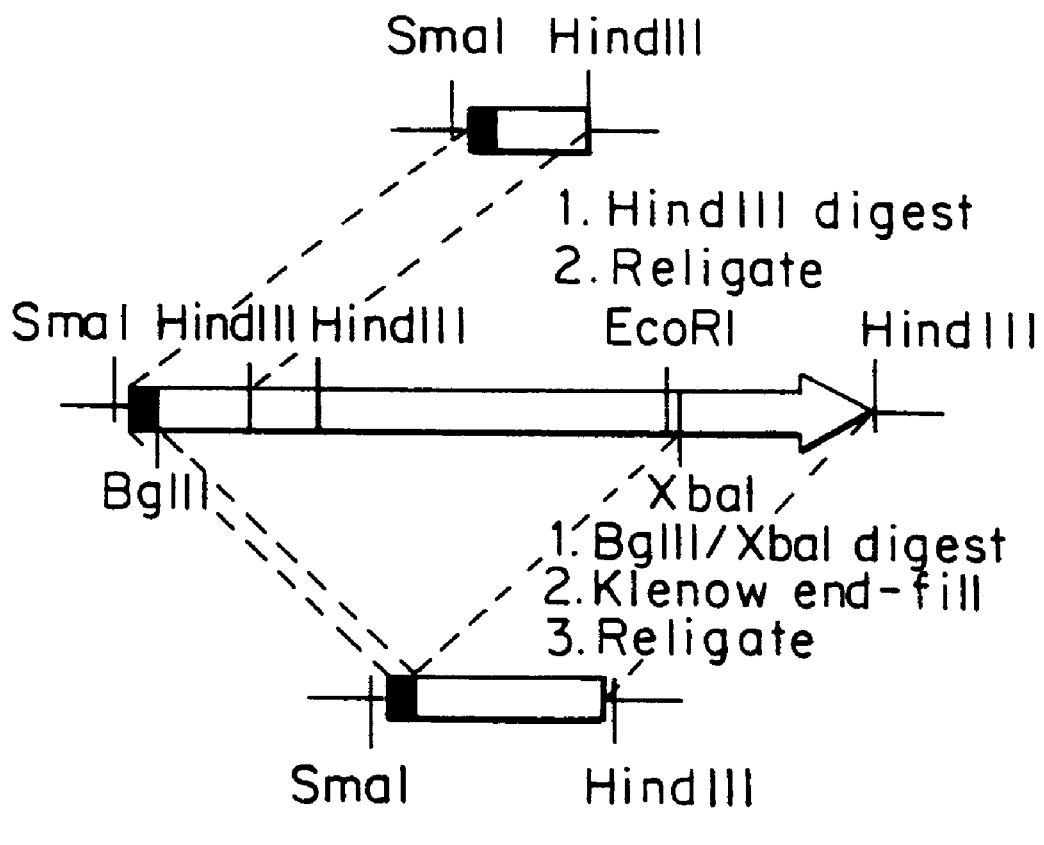

FIGS. 12A, 12B show the construction of CrFC21 and CrFC26 hybrid cDNA and its deletion mutants in the yeast expression plasmid, pEMBLyex4 (Caserini, G. and Murray, J. A. H., pp. 135–154 in "Genetic Engineering, Principles and Methods, vol. 9, eds. J. K. Setlow and A. Hollander, c. 1987 by Plenum Publishing Corp., New York, N.Y.; vector DNA was kindly provided by J. A. H. Murray). In FIG. 12A, the 1003 bp EcoRI/SalI fragment (containing the ribosomal binding site and initiation codon) of CrFC21 cDNA was excised from the EcoRI-flanking fragment of pCrFC21EE (also referred to as pEE21, U.S. Ser. No. 08/296,014 at FIG. 13) and cloned into the EcoRI and SalI sites of the plasmid pbluescript II SK- yielding the plasmid pBES21. This fragment was excised from pBES21 using SmaI and SalI digestion and introduced into SmaI/SalI digested pFC26Δ9a (pEMBLyex4/CrFC26Δ9a—see U.S. Ser. No. 08/296,014) to give pFC21/26. FIG. 12B shows the deletion mutant pFC21/26-H3 which was created by digesting pFC21/26 with HindIII, thus removing 2286 bp of 3' sequences, followed by religation of the plasmid. Internal deletion of 2257 bp fragment by double digestion of pFC21/26 with BglII and XbaI, and subsequent ligation of their filled ends produced the deletion mutant, pFC21/26-BX.

Figure 13:
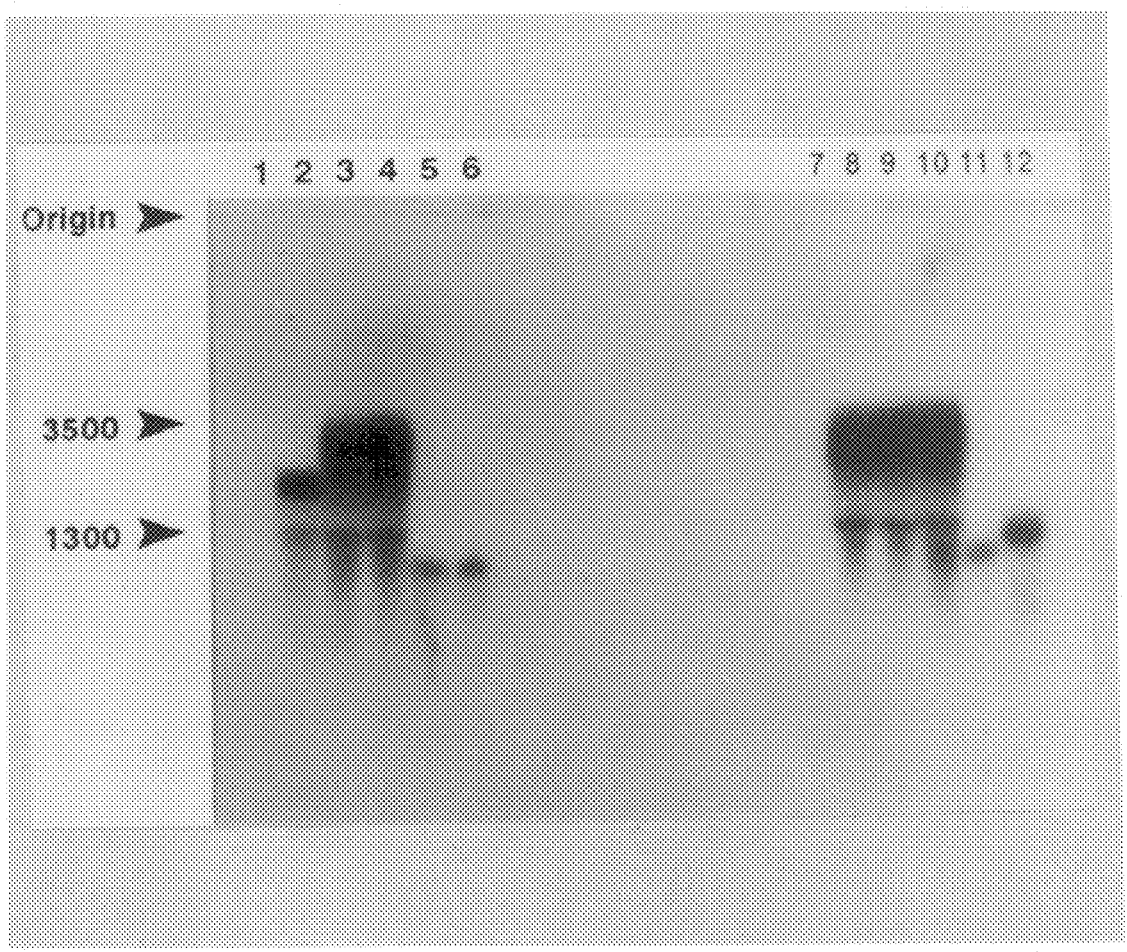

FIG. 13 shows Northern analysis of Factor C transcripts from S. cerevisiae. Varying sizes of the Factor C cDNAs were inserted into both pEMBLyex4 and YepSec1 vectors (see FIG. 9 and Table 1) with a view to investigating the relationship of the size of the inserts in the constructs to transcription level and mRNA structure in the S. cerevisiae host. RNA isolated from various clones after 18 hours of galactose induction were electrophoresed, blotted and hybridized with $^{32}$P-CrFC probes:

| Lane | Construct | size (bp) | mRNAs (kNt) |
|---|---|---|---|
| 1 | Yepsec1 DNA (control) | — | — |
| 2 | YFC26SP | 1902 | 2.1, 1.3 |
| 3 | YFC26Δ6a | 3447 | 3.5, 1.3 |
| 4 | YFC26Δ9a | 3492 | 3.5, 1.3 |
| 5 | YFC26Δ6a-H3 | 543 | 0.9 |
| 6 | YFC26Δ9a-H3 | 588 | 0.9 |

-continued

| Lane | Construct | size (bp) | mRNAs (kNt) |
|---|---|---|---|
| 7 | pEMBLyex4 DNA (control) | — | — |
| 8 | pFC26Δ6a | 3447 | 3.5, 1.3 |
| 9 | pFC26Δ9a | 3492 | 3.5, 1.3 |
| 10 | pFC21/26 | 3448 | 3.5, 1.3 |
| 11 | pFC21/26-H3 | 535 | 0.9 |
| 12 | pFC21/26-B/X | 1191 | 1.2 |

Figure 14:
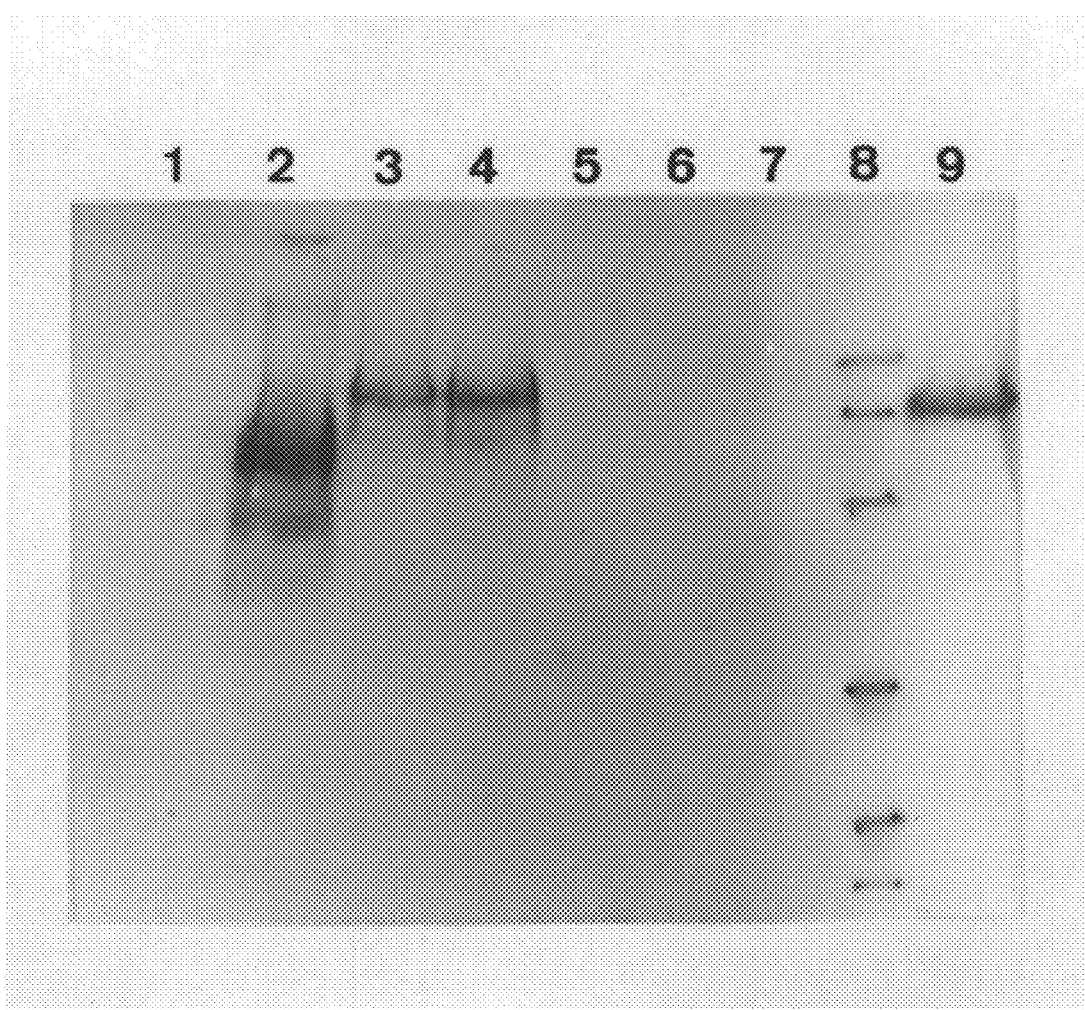

FIG. 14 shows the Western analysis of rCrFC from various S. cerevisiae clones containing (1) YepSec1 vector, (2) YFC26SP, (3) YFC26Δ6a, (4) YFC26Δ9a, (5) YFC26Δ6a-H3, (6)YFC26Δ9a-H3, (7) DNA from untransformed S. cerevisiae and (9) pFC21/26 hybrid clone. The molecular weight markers (215, 137, 71, 42, 31, 17.9 kDa) are in lane 8. The yeast cells were lysed directly in 50 mM Tris-Cl, pH 8.0, containing 0.1 M NaCl and 1% SDS.

Figure 15:
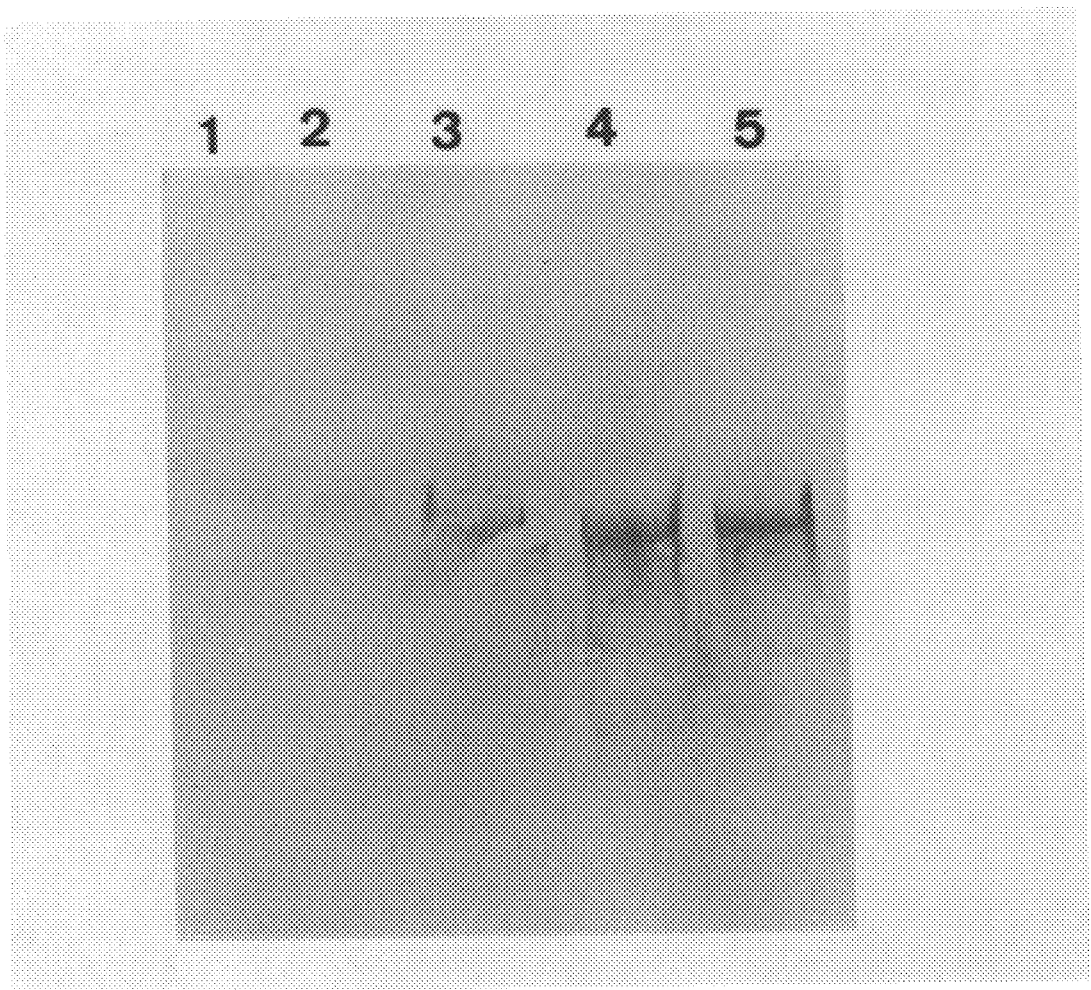

FIG. 15 shows the Western analysis of rCrFC from a S. cerevisiae clone containing pEMBLyex4/CrFC21. The rCrFC is ~130 kDa. Treatment of particulate rCrFC with SDS at 0% to (lanes 1,2); 0.5% (lane3) and 1 (lanes 4 & 5) showed increasing solubilization of rCrFC with increasing SDS concentration.

Figure 16A:
Figure 16B:

FIGS. 16A, 16B. FIG. 16A shows solubilization of rCrFC in SDS; FIG. 16B shows solubilization of rCrFC in Triton X-100. Induced pFC21/26 yeast transformants were lysed in 0.1 M NaCl, 50 mM Tris-Cl, pH 8.0 containing (1) 0%, (2) 0.5%, (3) 1.0%, (4) 2.0%, (5) 3.0%, (6) 4.0%, and (7) 5.0% SDS. The same transformants were lysed in (1) 0%, (2) 0.05%, (3) 0.1%, (4) 0.5%, (5) 1.0%, (6) 2.0%, (7) 4.0%, (8) 5.0% Triton X-100. For comparison, lane (9) contained 1.0% SDS-solubilized lysate. Molecular weight markers are in lanes 8 and 10, respectively, of gels shown in FIGS. 16A and 16B.

Figure 17:
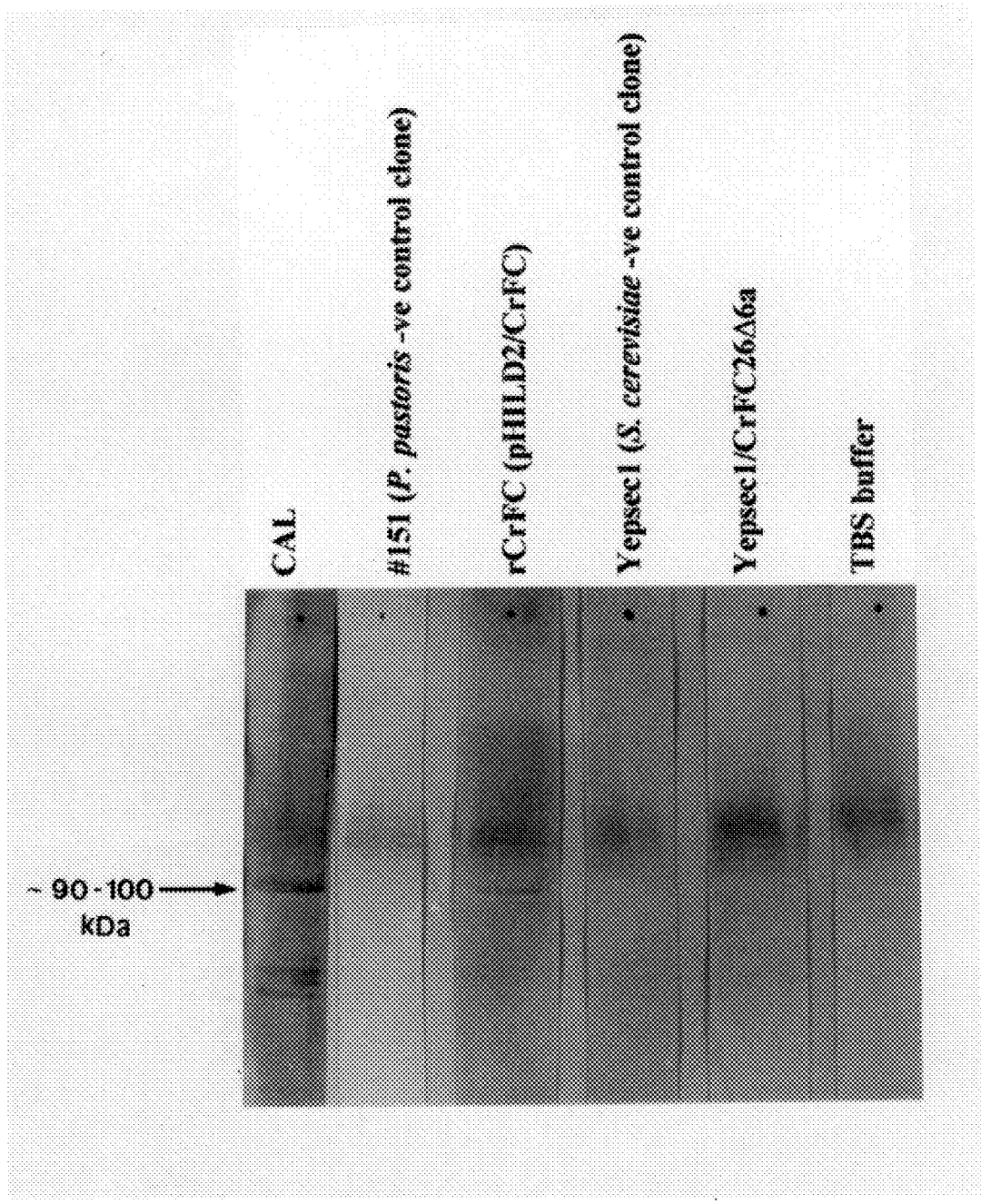

FIG. 17 shows evidence for the binding of SDS-solubilized rCrFC (from both full-length and truncated CrFC constructs in P. pastoris and S. saccharomyces to endotoxin that has been immobilized on a PVDF membrane. LPS-strips were obtained by electrophoresis of LPS (10 μg per lane) on SDS-polyacrylamide gels (15%). After electroblotting, the membrane was cut into strips (hence, LPS-strips), and each strip was incubated overnight at 37° C with 200 μg (total crude protein) of the respective protein sample. A band of ~90–100 kDa is seen in rCrFC samples, corresponding to that of Carcinoscorpius rotundicauda amoebocyte lysate (that contains Factor C) that has complexed with endotoxin on the LPS strip. The LPS-strips incubated with the rCrFCs showed a lower band which was not present on the LPS-strips incubated with the negative controls (P. pastoris, #151 and S. cerevisiae harboring only the vector, pEMBLyex4).

DETAILED DESCRIPTION OF THE INVENTION

The present invention resides in part in the development of efficient systems for production of rCrFC in vivo. The present inventors have found that rCrFC is effectively produced in eukaryotic cells, especially yeasts. In particular, yeasts of the genus Saccharomyces and Pichia are shown to be effective cells for expressing cDNA encoding CrFC.

The rCrFC of the present invention can be purified from cultures of recombinant eukaryotic cells expressing the protein by solubilizing the rCrFC, then proceeding essentially as described in co-pending application U.S. Ser. No. 08/296,014. The solubilization is preferably performed using a detergent solution. The detergent used is preferably anionic or non-ionic.

Alternatively, the rCrFC can be purified by affinity methods using an anti-Factor C antibody or gram-negative LPS as the affinity reagent. Methods for affinity purification of proteins are well-known in the art. General protein purification methods are also described in the art. The practitioner is referred to, for example, the "Guide to Protein Purification, published as volume 182 of Methods in Enzymology, M. P. Deutscher, editor, c. 1990 by Academic Press, Inc., San Diego, Calif.

For preservation of the rCrFC in the proenzyme state, $Me_2SO$ is preferably added to media used in the purification. Also, it is sometimes advantageous to add chelators of divalent metal ions, especially such as citrate, EDTA or EGTA.

The rCrFC of the present invention can be used in a method for removing endotoxin from a liquid sample, such as a parenteral preparation or a medium for in vitro culture of cells, by immobilizing the rCrFC on a suitable insoluble substrate to form immobilized rCrFC. The immobilized rCrFC is then contacted with the liquid sample under conditions favorable to binding of endotoxin in the sample to the immobilized rCrFC, thereby forming bound endotoxin. The bound endotoxin is then separated from the sample to provide a preparation from which the endotoxin has been removed.

It is expected that gram-negative bacterial endotoxin will bind to rCrFC under conditions of moderate pH, such that neither the rCrFC nor the endotoxin is denatured. The pH will preferably range from 6 to 9, most preferably at pH 7 to 8. Furthermore, it is expected that the binding of rCrFC to endotoxin can occur over a wide range of ionic strength, at least up to that equal to a 0.5 M NaCl solution. Preferably, the ionic strength is equal to a solution of salt in the range of 0.010 to 0.2 M, most preferably in the range of 0.050 M to 0.2 M. Because the rCrFC retains its immunoreactivity with anti-Factor C antibody even in the presence of substantial amounts of detergent, it is expected that endotoxin will bind to rCrFC even in the presence of low concentrations of chaotropic agents. Also, the rCrFC-endotoxin complex formation is not disrupted by the presence of substantial amounts of non-specific proteins in the solution. The sample is treated with sufficient immobilized rFc and for such time as necessary to remove the endotoxin to provide a sample substantially free of endotoxin. The amount of endotoxin removed is most preferably 99.9% of the endotoxin initially present. However for some applications, it will suffice to remove 85 to 99% of the endotoxin initially present in the sample. In still other applications, it might suffice to remove 80 to 90% of the endotoxin from the sample.

The rCrFC can be attached to an insoluble substrate by any of the methods for covalent attachment of a protein to insoluble substrates well-known in the art, for example by reaction with cyanogen-bromide activated agarose beads. Also, non-covalent methods can be used for immobilizing the rCrFC, for example by conjugation with biotin and subsequent immobilization on an avidin-conjugated bead.

For use in batch extraction procedures, immobilization on a bead is preferred. For use in continuous processing formats, immobilization in hollow fibers or on membranes, for stacking into cartridge formats, is preferred.

The rCrFC of the present invention also provides a method for specific detection of endotoxin in a sample by a method similar to ELISA or other immunoassay. For such an assay, the proteins in the sample are immobilized, for example by electroblotting to a membrane after separation by SDS-PAGE, or non-specific binding of proteins to a plastic substrate such as a microplate, and then endotoxin in the sample is detected by binding rCrFC to the immobilized endotoxin and subsequent detection of the rCrFC-endotoxin complex. The complex is detected either by measuring the serine protease activity of the bound rCrFC, for example by use of a chromogenic substrate assay, or by immunodetection with an anti-Factor C antibody. The endotoxin-rCrFC complexation step of such an assay can be performed under conditions similar to those for forming the complex for removing endotoxin from a sample as described above.

Although rCrFC is immunoreactive, and also capable of binding LPS (in an in vitro assay), its endotoxin-triggered enzymatic activity can be assessed by the following methodology.

Detergent (SDS, Triton X-100 or sarkosyl) solubilized rCrFC can be immobilized, preferably onto a membrane (e.g., IMMOBILON PVDF, Pall NYTON, nitrocellulose, ULTRABIND), followed by stepwise, gradual removal of the detergent from the membrane while allowing rCrFC to remain bound. This concurrently exposes the catalytic site of the Factor C enzyme. Removal of the detergent (the presence of which can interfere with the biological activity) enables the subsequent assay of endotoxin-activated serine protease activity of the rCrFC either by fluorometric or colorimetric methods.

This method is based on the rationale that detergents like SDS and Triton X-100 at certain percentage have been reported to inhibit LPS-activated serine protease activity of Factor C (Nakamura, T., Tokunaga, F., Morita, T. and Iwanaga, S., *J. Biochem.* 103:370–374 (1988)).

The invention being thus generally described, preferred embodiments of the invention are set forth in the Examples below. The Examples are not limiting of the invention. The scope of the invention is limited only by the claims recited below.

EXAMPLE 1

Figure 1:
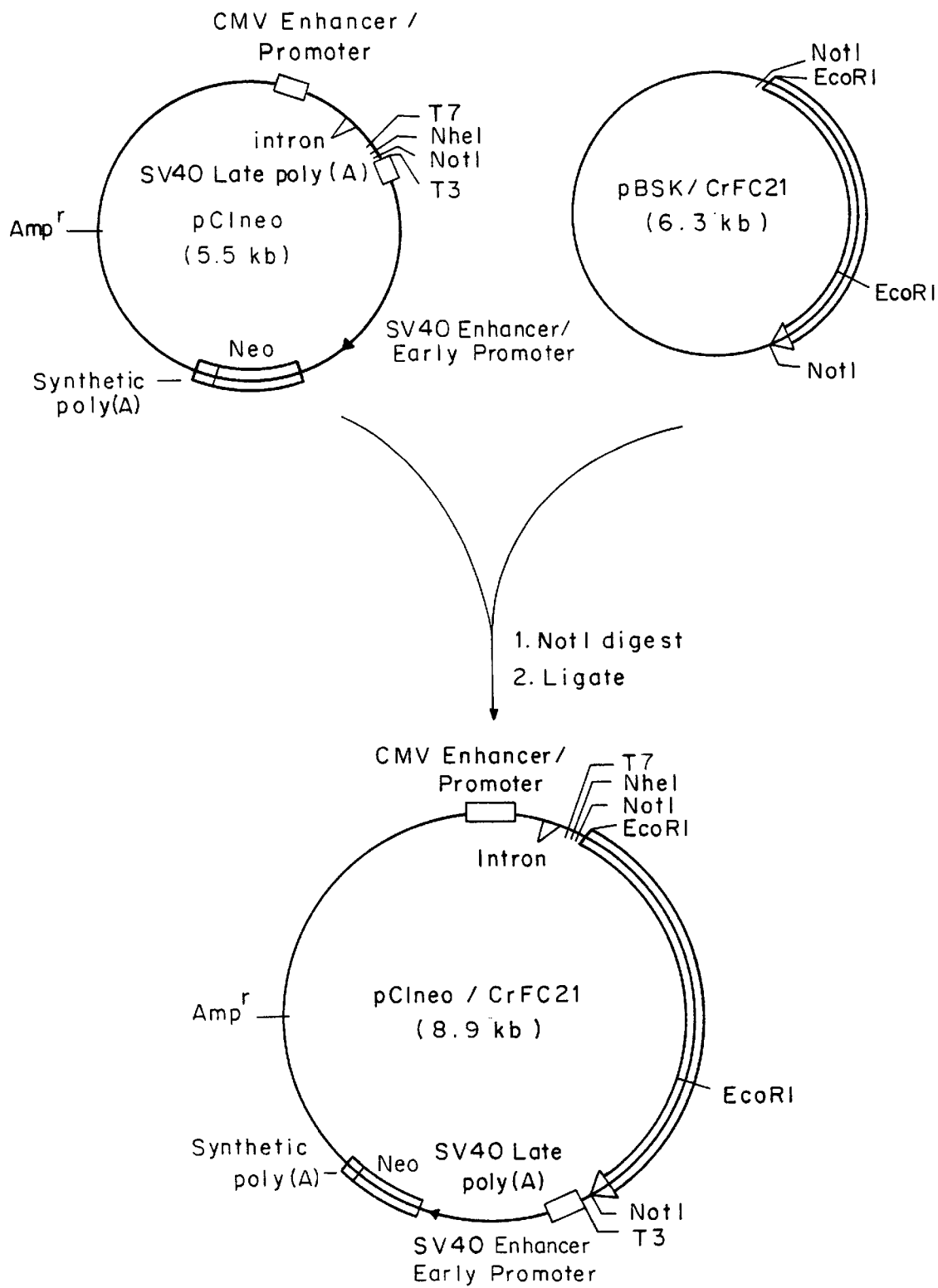
FIG. 1 shows the construct pCIneo/CrFC21, where the NotI flanking CrFC21 cDNA from pBluescript SK (pBSK/CrFC21) was cloned into the NotI site of pCIneo (Promega Corp., Madison, Wis.).

Cloning of CrFC21 cDNA into the Mammalian Expression Vectors pCDNA1 and pCIneo The CrFC21 cDNA cloned into a pCIneo vector provides a construct referred to as pCIneo/CrFC21 (FIG. 1). In this vector, constitutive expression in vivo of CrFC21 is driven by a CMV promoter. In vitro transcription can also be performed using the T7 promoter resident in the vector.

Figure 2:
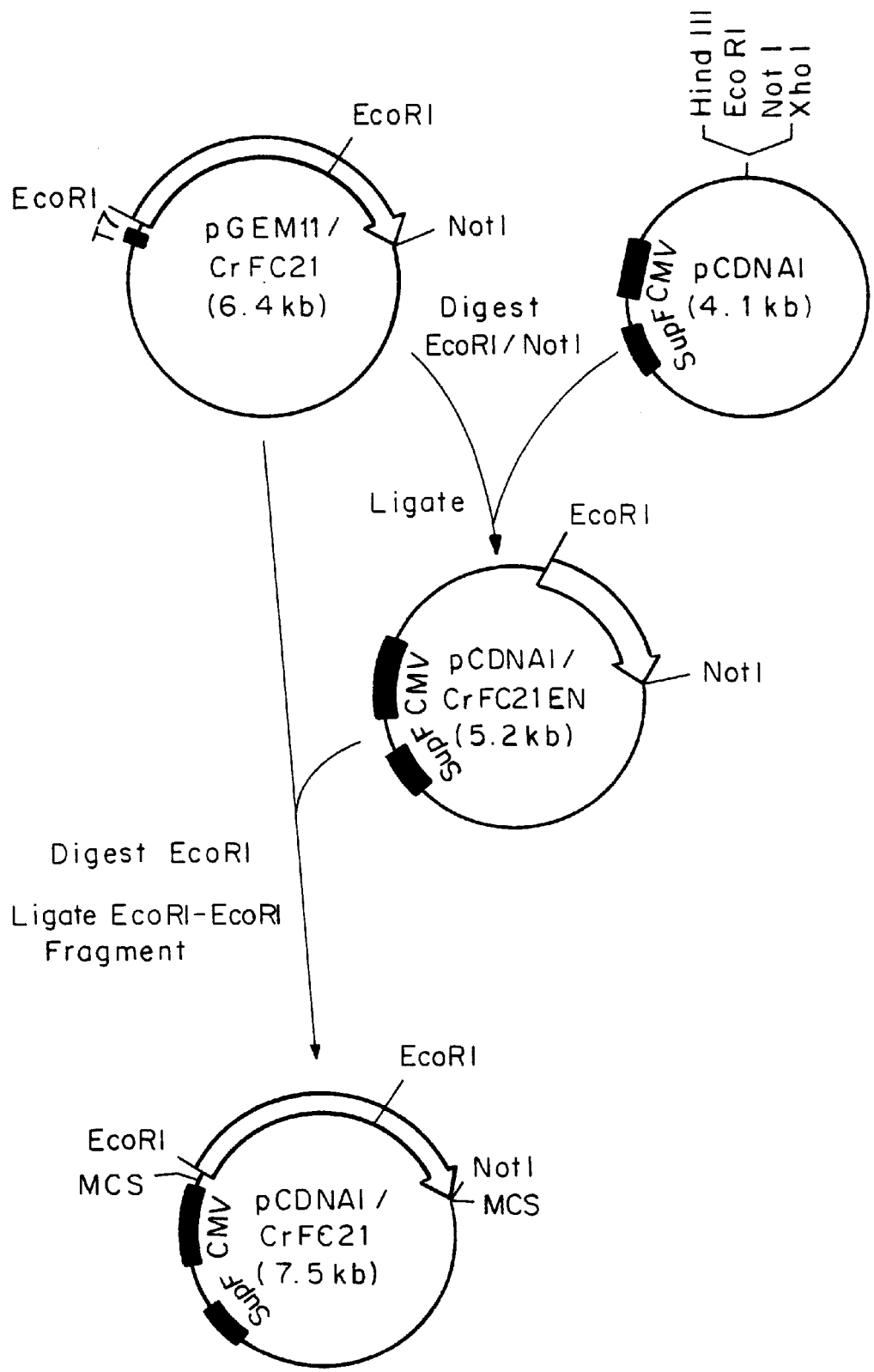
FIG. 2 shows the construct pCDNA1/CrFC21. The EcoRI-NotI fragment of CrFC21 derived from pGEM11Zf (+)/CrFC21 (see FIG. 13 of U.S. Ser. No. 08/296,014) was inserted into EcoRI-NotI digested parent vector pCDNA1 (InVitrogen Corp., San Diego, Calif.) to yield the construct pCDNA1/CrFC21EN. This was further digested with EcoRI to facilitate the inclusion of EcoRI flanking fragment of CrFC21 from pGEM11Zf(+)/CrFC21, thus recreating the full-length CrFC21 cDNA in the construct pCDNA1/CrFC21.

The CrFC21 cDNA was also cloned into pCDNA1, and henceforth referred to as pCDNA1/CrFC21 (FIG. 2). This construct was later used as an intermediate vector for construction of pHILD2/CrFC21 in *P. pastoris* expression system (see FIG. 4).

The pCIneo/CrFC21 and pCDNA1/CrFC21 constructs can be transfected into mammalian cell lines such as Chinese Hamster Ovary (CHO) cells, or mouse fibroblast cells such as NIH/3T3 cells, or Cos-1 cells or Hela cells, and used for expression of rCrFC. Transformation of the vectors into mammalian cells can be accomplished by means well-known in the art, for example, transfection by electroporation, or liposome-mediated gene transfer. Also, methods for culturing mammalian cells are generally well-known. Recovery of rCrFC produced by cultured mammalian cells can be performed substantially as described for purification from yeast cells, except that the physical disruption steps can be omitted, as mammalian cells lack a cell wall. Rather, intracellular rCrFC can be recovered by lysing the mammalian cells with detergents.

EXAMPLE 2

Expression of CrFC21 in *Pichia pastoris*

Constructs

Figure 3:
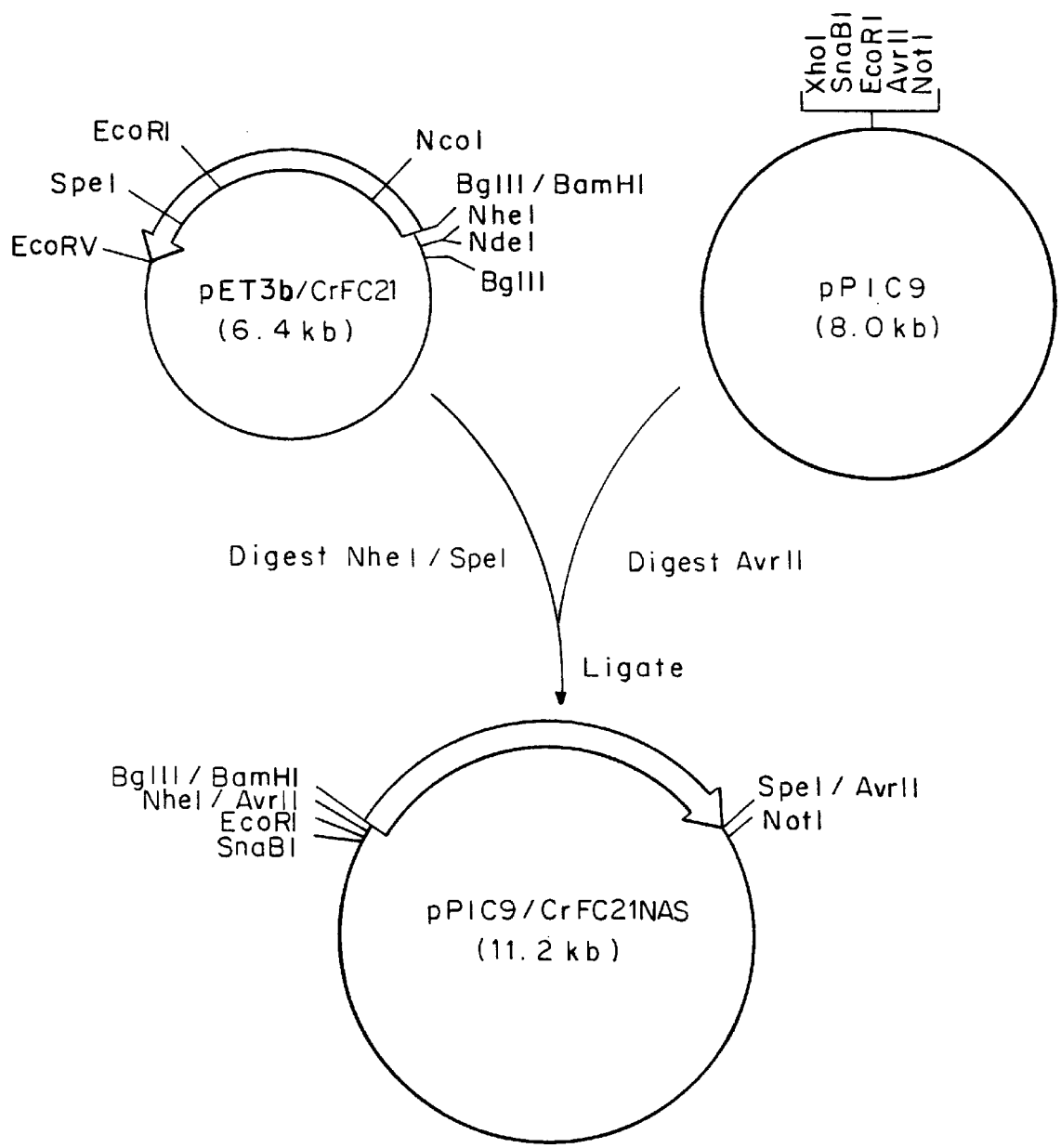
FIG. 3 shows the construct pPIC9/CrFC21NAS. The *P. pastoris* secretion vector, pPIC9 (InVitrogen Corp., San Diego, Calif.), was linearized with AvrII. The construct pET3b/CrFC21 (see FIG. 15 of U.S. Ser. No. 08/296,014) contains the BglII-EcoRV fragment of CrFC21 cDNA. (pET3b is commercially available from Novagen, Madison, Wis.). This cDNA was excised using NheI of the pET3b vector (upstream of the BglII/BamHI start) and SpeI (in the 3' untranslated region of CrFC21), giving a 3035 bp insert which was then fused in frame with the *S. cerevisiae* α mating factor signal peptide in the linearized pPIC9. The resultant construct is termed as pPIC9/CrFC21NAS. A short stretch of 11 amino acids belonging to the phage T7 gene 10 sequence (from *E. coli* expression vector pET3b, pAR3039) precedes the CrFC sequence.

The CrFC21 cDNA was inserted into two expression vectors of *P. pastoris*. The first is a secretory vector, pPIC9, where the CrFC cDNA was fused to the signal sequence of the a mating factor of *Saccharomyces cerevisiae* to yield the construct, pPIC9/CrFC21NAS (FIG. 3). This recombinant clone relies on the ATG codon present in PIC9 as the start codon. In PHILD2/CrFC21, the vector second is a non-secretory vector, pHILD2 providing the construct pHILD2/CrFC21 (FIG. 4). The host cell utilizes the native ATG of the CrFC cDNA insert as the start codon. In both cases, expression of the CrFC cDNA is driven by the AOX1 promoter, which is inducible by methanol.

Transformation of *P. pastoris*, Strain GS115 with CrFC Constructs

The pPIC9/CrFC21NAS was digested with StuI or BglII. The pHILD2/CrFC21 was digested with StuI. These linearized expression vectors were then transformed into *P. pastoris*, strain GS115 by the spheroplasting method (Cregg, J.M. et al., *Mol. Cell Biol.* 5x:, 3376–3385 (1985)). Isolation of mut$^s$ or mut$^+$ transformants was done according to described protocols (Clare, J. J. et al, *Bio/Technology* 9:455–460 (1991)).

Expression of Immunoreactive Recombinant Factor C in *P. pastoris*

The expression of CrFC21 constructs was studied in *P. pastoris* at the levels of transcription and translation. RNAs were purified from the cells after methanol-induction. To examine the production of recombinant Factor C (rCrFC) in the heterologous hosts, the transformants were cultured in shake-flasks, with ample aeration.

(i) Northern Analysis of pHILD2/CrFC21 Expression in *P. pastoris*

Various *P. pastoris* transformants of high gene-copy number were grown at 30° C. for 18 hours in 50 ml MGY medium (1.34% yeast nitrogen base, 1% glycerol, $4\times10^{-5}$% biotin to accumulate cell mass. The $OD_{600}$ reached 4 Units. The transformants were then transferred into 200 ml of MM medium (1.34% yeast nitrogen base, 0.5% methanol, $4\times10^{-5}$% biotin) giving an initial $OD_{600}$ of 1 Unit.

Figure 5B:
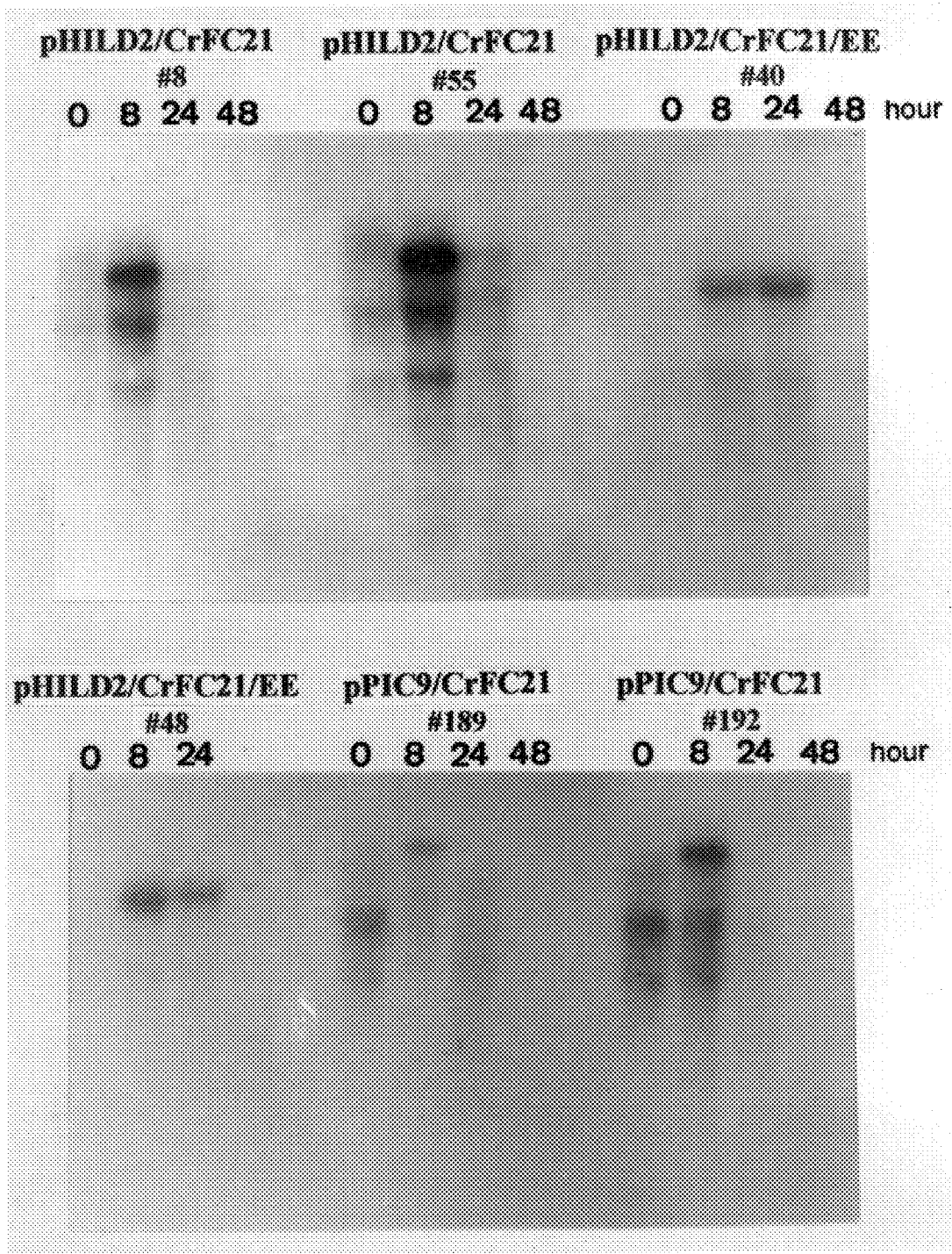
FIG. 5B shows Northern hybridization of Factor C transcripts from induced transformants (mut$^+$) of *P. pastoris* (GS115) containing pHILD2/CrFC21. The EcoRI-EcoRI flanking fragment of CrFC21 was $^{32}$P-labelled to high specific activity and used as probe for the Northern blot. The level of transcription was studied in 4 different clones at various time intervals of induction with 0.5%. methanol.

To examine the optimum transcription efficiency during methanol induction, replicate cultures of *P. pastoris* containing pHILD2/CrFC21 were induced for varying lengths of time and harvested by centrifugation at 3000×g for 10 minutes the cells were used for isolation of RNA under standard RNase-free conditions and Northern analysis was carried out (FIG. 5).

(ii) Western Analysis of rCrFC Obtained from *P. pastoris* Clone #8 (pHILD2/CrFC21)

The methanol-induced cells were pelleted and resuspended in 1:10 (v/v) with breaking buffer (0.05 M Tris-HCl1, pH 8.0, containing 0.1 M NaCl) and added with an equal volume of chilled, acid-washed glass beads (0.45 mm diameter, Sigma). The cells were lysed by vortexing for 1 min and chilled on ice for 3 min. This process was repeated 9 times or until complete breakage of the cells was observed. The soluble and insoluble fractions were separated by centrifugation at 10,000×g for 30 min. at 4° C. After resuspending the pellet in breaking buffer containing SDS ranging in concentration from 0.5–5%, overnight extraction was carried out at 4° C. on a rotary platform. The soluble intracellular fraction, the SDS-solubilized cell extract, and the supernatant derived from the culture media of pHILD2/CrFC21 clones were resolved on 10% PAGE gels under reducing conditions of SDS/β-mercaptoethanol, and electroblotted for Western analysis. FIG. 6 shows that the clones produced rCrFC during the 8 hours after methanol induction. The rCrFC was produced within the host cell in an insoluble form, and was solubilized optimally by 1% SDS.

With clone #8 (pHILD2/CrFC21) studied over closer time points it was confirmed that 8 hours post-induction was the optimum timing of rCrFC protein synthesis (FIG. 7).

(iii) Detergent Solubilization of rCrFC from *P. pastoris* (pHILD2/CrFC21, Clone #8)

Triton X-100, SDS and sarkosyl were used at a range of concentrations to solubilize rCrFC from the recombinant *P. pastoris* clones. Cells from clone #8 were harvested after 8 hours of methanol induction, centrifuged, and the cell pellet was treated with glass beads (as described earlier). Cell homogenates were made up to their respective (w/v) percentage of detergent, and solubilized overnight at 4° C. by rotation on an angular rotator. The lysate was cleared by centrifugation. The supernatant which contains solubilized rCrFC constitutes approximately 30–50% of the total rCrFC. The pellet still contains a large amount of insoluble rCrFC. Western analysis showed maximal solubilization of rCrFC at 1% SDS (FIG. 8A), and 1% sarkosyl (FIG. 8B). These detergent-solubilized rCrFC's have retained their immunoreactivity.

EXAMPLE 3

Expression of Recombinant Factor C in *Saccharomyces cerevisiae*

Constructs

By manipulation of the 5' end of CrFC26, truncated constructs containing this cDNA are expressed by *S. cerevisiae* to give immunoreactive rCrFC. The rCrFC produced from both CrFC21 and CrFC26 constructs is solubilized by Triton X-100 and SDS, and found to be immunoreactive. Solubilized rCrFC could thus be purified as a proenzyme and reversibly protected from activation by addition of $Me_2SO$ (see U.S. Ser. No. 08/296,014).

The full-length CrFC26 cDNA has earlier been cloned into both YepSec1 and pEMBLyex4 expression vectors of *S. cerevisiae* (see U.S. Ser. No. 08/296,014 at FIG. 16). Updated nomenclature of the CrFC26 cDNA constructs in these two vectors are shown in FIG. 9 and Table 1. The long 5' untranslated region (UTR) of CrFC26 suggests that it may play a role in regulating the expression of the gene at the translational level. Studies using a coupled in vitro transcription and translation system surprisingly showed no expression of rCrFC from CrFC26. On the other hand CrFC21, which lacks the long 5' non-coding sequence, expressed rCrFC at high levels (see, FIG. 18 of U.S. Ser. No. 08/296,014). This indicates that the 5' non-coding sequence serves to down-regulate the translation of CrFC26. In order to express CrFC26 in a heterologous system, it is preferred that the 5' UTR be removed, at least to the point where its translation-attenuating activity is reduced or eliminated. A deletion mutant library made by 5'–3' ExoIII deletion mutagenesis of the EcoRI-EcoRI (EE) fragment yielded two subclones designated FC26Δ6a and FC26Δ9a (FIG. 10). Further deletions of these subclones at HindIII (position 1278) removed sequences downstream, giving rise to FC26Δ6a-H3 and FC26Δ9a-H3, respectively. These deletion mutant were cloned into the YepSec1 vector and the constructs were transformed into *S. cerevisiae* for expression analyses. These subclones were selected based on the creation of an open reading frame, which is attained upon religation of the deleted ends to the vector (FIGS. 11A, 11B). The DNA sequences at the junctions between the vectors and FC26Δ6a and 9a were verified by sequencing, and found to be in-frame (FIG. 11A). These constructs will utilize the ATG codon within the SphI site of the vector for translation initiation.

FIG. 12A shows a hybrid cDNA consisting of the 5' portion of CrFC21 and the 3' portion of CrFC26, inserted into pEMBLyex4. This was done by substituting the SmaI-SalI fragment of pFC26Δ9a (pEMBLyex4/CrFC26Δ9a) with the SmaI-SalI fragment isolated from pBES21 to give pFC21/26 (pEMBLyex4/CrFC21/26). At the amino acid level, the fusion gene product would be expected to be identical to the product encoded by CrFC21 except for a single Arg to Ser substitution at residue 427 of CrFC21. Translation initiation in pFC21/26 would rely on the cognate ATG codon of CrFC21. FIG. 12B shows deletion mutant constructs of this hybrid cDNA.

Various fragments of CrFC26 cDNA (FIG. 10) were also subcloned into the *S. cerevisiae* secretory expression vector, YepSec1. Also the CrFC21 and CrFC26 hybrid cDNAs and deletion mutants thereof were recloned in the yeast expression plasmid, pEMBLyex4 (FIG. 12). Expression of cDNA from pEMBLyex4 is expected to result in intracellular accumulation of the product. The *S. cerevisiae* host strain, S150-2B was used as a host cell for the constructs. Table 1 summarizes the CrFC cDNA constructs in pEMBLyex4 and YepSec1 vectors.

TABLE 1

*Carcinoscorpius rotundicauda* Factor C gene constructs in the *S. cerevisiae* expression plasmid vectors, YepSec 1 (secretory) and pEMBLyex4 (non-secretory)

| Vector | Construct Name | Insert | Yeast Host Strains Transformed and Conserved |
|---|---|---|---|
| YepSec1 | Yepsec1 | Nil | 150-2B |
| | YFC26Δ6a | Deletion clone CrFC26 6a | 150-2B |
| | YFC26Δ9a | Deletion clone CrFC26 9a | 150-2B |
| | YFC26Δ6a-H3 | Deletion clone CrFC26 6a - Hind III | 150-2B |
| | YFC26Δ9a-H3 | Deletion clone CrFC26 9a - Hind III | 150-2B |
| | YFC26SP | Sal I-Pst I of CrFC26 | 150-2B |
| pEMBLyex4 | PEMBLyeX4 | Nil | 150-2B |
| | pFC26Δ6a | Deletion clone CrFC26 6a | 150-2B |
| | pFC26Δ9a | Deletion clone CrFC26 9a | 150-2B |
| | pFC21/26 | CrFC21-CrFC26 Hybrid | 150-2B |
| | p21/26-B/X | CrFC21-CrFC26 Hybrid - Bgl II/Xba I | 150-2B |
| | p21/26-H3 | CrFC21-CrFC26 Hybrid - Hind III | 150-2B |

Transformation of S. cerevisiae, Strain S150-2B with CrFC cDNA Constructs

The S. cerevisiae strain S150-2B (leu2 his3 ura3 trpl) was used for transformation by a modified lithium acetate procedure (Schiestl, R. H. and Gietz, R. D., 1989. Current Genetics 16:339–346 (1989)). Transformed yeast cells were recovered by selection on uracil-deficient synthetic complete medium (SC-ura) (Sherman, F. et al, in "Methods in Yeast Genetics" c. 1979 by Cold Spring Harbor Laboratory, Cold Spring, Harbor, N.Y.) containing 2% glucose and 0.67% yeast nitrogen base (YNB) without amino acids (Difco) and supplemented with the required amino acids.

Expression of rCrFC in S. cerevisiae (i) Induction of Factor C Synthesis

Yeast cells harboring secretory plasmids were cultured at 30° C. in complex YPD medium (1% yeast extract, 2% peptone and 2% glucose) to late log phase upon which the cells were induced by supplementing the medium with 2% galactose. For the induction of intracellular Factor C expression, recombinant yeasts were first cultured in SC-ura medium supplemented with 40 µg/ml leucine. At late log phase, cells were harvested and resuspended in fresh SC-ura medium containing 60 µg/ml leucine and 2% galactose. The induced cells were harvested for protein analyses following 24 hours growth at 25° C.

(ii) Transcription of Recombinant CrFC cDNA in S. cerevisiae

Total yeast RNA was prepared from induced yeast cells. RNA samples were denatured with glyoxal and dimethyl sulfoxide, and fractionated on a 1.2% agarose gel. Following transfer to nylon filters, the RNA was hybridized against pooled $^{32}$P-labelled CrFC/EE21 and CrFC/EN21 fragments. Hybridized filters were subjected to autoradiography (FIG. 13).

FIG. 13 shows the results of the Northern blot analysis. Varying sizes of the Factor C cDNAs were inserted into both pEMBLyex4 and YepSec1 vectors (see FIG. 10 & Table 1) with a view to investigating the size limitation of the constructs to transcription level in the S. cerevisiae. RNA isolated from various clones after 18 hours galactose induction were electrophoresed, blotted and hybridized with 32P-CrFC probes:

Transcription of the constructs does not appear to be limited by the size of the insert in the construct. In fact, the constructs having larger, more full length inserts exhibit two transcripts. The larger, major transcript of 3.5 kb (lanes 3, 4, 8, 9 & 10) corresponds to the expected full length CrFC mRNA. The smaller, minor mRNA of 1.3 kb could be CrFC transcript expressed via the use of internal alternative polyadenylation signal (lanes 2, 3, 4, 8, 9 & 10) or internal transcription initiation. Internal TATA boxes are present in both CrFC21 and 26. With CrFC21, two of these elements, located at regions corresponding to nucleotide positions 1823–1827 and 3105–3110 could have yielded the ~1.3 kb transcript when induced in yeast cells.

(iii) Extraction of rCrFC and Western Analyses

Yeast cells were collected from 10 ml induced cultures and respended in 0.2 ml of disruption buffer, containing 25 mM Tris-Cl, ph 8.0 and 0.1 M NaCl with or without SDS or Triton X-100. For solubilization of insoluble proteins, (a) SDS was added to the samples to a final concentration of 0.5, 1, 2, 3, 4, and 5%; and (b) Triton x-100 was added at 0.05, 0.1, 0.5, 1, 2, 4 and 5%. An equal volume of chilled, acid washed glass beads (0.45 mm, Sigma) was added to the cell suspension. Cells were disrupted by vortexing 5 times for 1 min each, with 5 minute intervals of chilling in between vortexing. Cells were checked for complete lysis by examination under the microscope. Lysates were clarified by centrifugation at 17,600×g for 1 h. Protein extracts were electrophoresed on denaturing SDS/10% polyacrylamide gel, and blotted onto pvdf membrane (Millipore) by electrotransfer. Rabbit anti-Factor C antibody was used as the primary antibody. The immunoblot was developed with horseradish peroxidase conjugated goat anti-rabbit antibody using 4-chloro-1-naphthol and hydrogen peroxide as substrates.

(iv) Expression of rCrFC from YepSec1 Plasmid Constructs

With YFC26sp, YFC26Δ6a and YFC26Δ9a transformants, cell lysates prepared by glass bead disruption showed substantial amounts of immunoreactive recombinant protein in the soluble, intracellular fractions (FIG. 14). It is evident from the results that the K. lactis killer toxin signal sequence did not direct the secretion of the recombinant product. No immunoreactive band was detected in YFC26Δ6a-H3 and YFC26Δ9a-H3.

Although transcripts were found for these deletion mutant (shortened) constructs (see FIG. 13), no translational products were evident (see FIG. 14). Three explanations may be given for this observation: (a) the transcripts were defective for translation, (b) the truncated rCrFC proteins were unstable, and underwent rapid in situ degradation, or (c) the truncated rCrFCs were synthesized but not immunoreactive that is, the deletions have removed the major epitopes of Factor C, thus abolishing immunoreactivity.

(v) Expression of rCrFC from pEMBLYex4 Plasmid Constructs

A single immunoreactive band with an apparent size of ~135 kDa was observed for cell lysates of pEMBLyex4/CrFC21 transformants only (FIG. 15). This recombinant protein is approximately 11 kDa larger than the calculated size based on the cDNA insert length. This may be attributable to glycosylation of the protein. In eukaryotic cells, glycosylation is usually coupled to secretion of the product. However, it has been found that in horseshoe crabs, the amoebocyte Factor C is glycosylated, but not secreted. Rather, the glycosylated Factor C is found in intracellular granules. Immunogold electron microscopy studies are being performed to confirm the localization of the rCrFC produced by the pEMBLyex4/CrFC21 transormants. Contrary to full length CrFC cDNA clones, no detectable immunoreactive protein was observed in lysates from partial subclones such as pFC21/26-H3 and pFC21/26-BX transformants (FIG. 12B).

Increasing SDS concentration provided better solubilization up to 1% SDS. SDS at 1% appears to yield maximum solubilization. Further increase in SDS concentrations up to 5% did not improve the yield of the recombinant protein (FIG. 16A). Similar efficiency of solubilization of rCrFC was observed with Triton X-100 (FIG. 16B).

EXAMPLE 4

Endotoxin-binding of rCrFC Derived from PHILD2/CrFC21 and pHILD2/CrFC21EE

Endotoxin-binding activity of rCrFC is shown as described herein. 10 µg of E. coli LPS (Sigma, St. Louis, Mo. (E. coli O55B)) is electrophorectically separated on SDS-PAGE (15%) followed by electroblotting of the resolved LPS onto to a PVDF membrane. The membrane blot was blocked by incubating in 50 mM Tris-HCl, pH 8 containing 0.2 M NaCl (Tris buffered saline, TBS) with 30 mg/ml BSA for 30 min. at 37° C. The membrane was cut into strips (LPS strips) and each strip was separately incubated overnight with slight agitation at 37° C. with 200 μg total protein of crude solubilisate of rCrFC. The strips were then washed 3× for 5 min. each with TBS before incubation for 3 h at 37° C. with anti-Factor C antibody diluted 500× in TBS containing 1 mg BSA. Subsequently, the strips were washed with TBS followed by incubation for 1 h at 37° C. with peroxidase-conjugated goat anti-rabbit IgG in TBS with 1 mg/ml BSA. After rinsing extensively, the strips were stained with 60 μl H$_2$O$_2$ and 60 mg chloro-1-napthol (Sigma) in 20% methanol (v/v).

FIG. 16 shows evidence for the binding capability of SDS-solubilized rCrFC (derived from PHILD2/CrFC21, clone #8) for endotoxin as compared with that of the *Carcinoscorplus rotundicauda* amoebocyte lysate (CAL which contains native Factor C).

The invention being thus described, various modifications of the materials and methods used in practice of the invention will be readily apparent to one of ordinary skill in the art. Such modifications are considered to be encompassed by the scope of the invention as it is described in the claims below.

---

What is claimed is:

1. A method for removing endotoxin from a liquid sample comprising:
   i) immobilizing a recombinant Factor C protein of a horseshoe crab, or a variant or portion thereof having endotoxin-binding activity, produced in a yeast, to provide immobilized Factor C;
   ii) contacting said immobilized Factor C with said liquid sample, under conditions favorable to binding of endotoxin in said sample to said immobilized Factor C, to form bound endotoxin; and
   iii) separating said bound endotoxin from said sample, to provide a sample substantially free of endotoxin.

2. A method for detecting endotoxin in a sample, which comprises:
   i) immobilizing proteins present in said sample;
   ii) contacting the immobilized proteins with recombinant Factor C of a horseshoe crab, or a variant or portion thereof havinq endotoxin-binding activity, produced in a yeast, to form an endotoxin-Factor C complex; and
   iii) detecting said endotoxin-Factor C complex.

3. The method of claim 2, wherein the endotoxin-Factor C complex is detected by immunodetection of the Factor C.

4. A recombinant Factor C protein produced by a method comprising:
   i) transforming a yeast cell with an expression vector comprising a DNA fragment encoding a Factor C protein of a horseshoe crab;
   ii) culturing said transformed yeast cell; and
   iii) recovering the recombinant Factor C protein produced by the cultured yeast cells.

5. The method of claim 1, wherein a recombinant Factor C having the amino acid sequences of SEQ. ID. NO.:2 or SEQ. ID. NO.:4, or a portion thereof having endotoxin-binding activity, produced in a yeast, is immobilized in step i).

6. The method of claim 2, wherein a recombinant Factor C having the amino acid sequences of SEQ. ID. NO.:2 or SEQ. ID. NO.:4, or a portion thereof having endotoxin-binding activity, produced in a yeast, is immobilized in step i).

7. The method of claim 1, wherein said immobilized Factor C has the amino acid sequence of SEQ. ID. NO.: 2 or SEQ. ID. NO.: 4.

8. The method of claim 2, wherein said immobilized Factor C has the amino acid sequence of SEQ. ID. NO.: 2 or SEQ. ID. NO.: 4.

* * * * *